(12) United States Patent
Keith et al.

(10) Patent No.: US 6,478,813 B1
(45) Date of Patent: *Nov. 12, 2002

(54) METHOD FOR JOINING GRAFTS IN A COMMON BODY PASSAGEWAY

(76) Inventors: Peter T. Keith, 1477 Grantham St., St. Paul, MN (US) 55108; Thomas V. Ressemann, 1730 Boxwood Cir., St. Cloud, MN (US) 56303

( * ) Notice: Subject to any disclaimer, the term of this patent is extended or adjusted under 35 U.S.C. 154(b) by 0 days.

This patent is subject to a terminal disclaimer.

(21) Appl. No.: 09/474,989

(22) Filed: Dec. 29, 1999

Related U.S. Application Data

(63) Continuation of application No. 08/904,977, filed on Aug. 1, 1997, now Pat. No. 6,070,589.

(51) Int. Cl.[7] ................................................. A61F 2/06
(52) U.S. Cl. ................... 623/1.11; 623/1.13; 623/1.23; 606/108; 128/898
(58) Field of Search ............................. 623/1.11, 1.13, 623/1.18, 1.12, 1.16, 1.23, 1.35, 1.36; 606/198, 108

(56) References Cited

U.S. PATENT DOCUMENTS

| | | |
|---|---|---|
| 3,304,557 A | 2/1967 | Polansky |
| 3,585,707 A | 6/1971 | Stevens |
| 3,657,744 A | 4/1972 | Ersek |
| 4,169,464 A | 10/1979 | Obrez |
| 4,187,390 A | 2/1980 | Gore |
| 4,317,451 A | 3/1982 | Cerwin et al. |
| 4,441,216 A | 4/1984 | Ionescu et al. |
| RE31,618 E | 7/1984 | Mano |
| 4,503,569 A | 3/1985 | Dotter |
| 4,553,545 A | 11/1985 | Maass |
| 4,562,596 A | 1/1986 | Kornberg |
| 4,580,568 A | 4/1986 | Gianturco |
| 4,604,762 A | 8/1986 | Robinson |
| 4,617,932 A | 10/1986 | Kornberg |
| 4,655,771 A | 4/1987 | Wallsten |
| 4,665,906 A | 5/1987 | Jervis |
| 4,681,110 A | 7/1987 | Wiktor |
| 4,705,517 A | 11/1987 | DiPisa, Jr. |
| 4,728,328 A | 3/1988 | Hughes |
| 4,731,073 A | 3/1988 | Robinson |
| 4,732,152 A | 3/1988 | Wallsten |
| 4,733,665 A | 3/1988 | Palmaz |

(List continued on next page.)

FOREIGN PATENT DOCUMENTS

| | | |
|---|---|---|
| DE | D3205942 A1 | 9/1983 |
| EP | 0 540 290 A3 | 5/1993 |
| EP | 0579523 A1 | 1/1994 |

(List continued on next page.)

OTHER PUBLICATIONS

Timothy A. M. Chuter, et al., "Transfemoral endovascular aorticgraft placement", Journal of Vascular Surgery, vol. 18, No. 2, (1993), pp. 185–197.

Calvin B. Ernets, M.D., "Abdominal Aortic Aneurysm", Current Concepts, Review Articles, vol. 328, No. 16, (Apr. 22, 1993), pp. 1167–1172.

*Primary Examiner*—Paul B. Prebilic
*Assistant Examiner*—William H Matthews

(57) ABSTRACT

A method for endoluminally treating a pathological defect is disclosed using grafts having a shape memory alloy disposed along their length. The method comprises the steps of introducing first and second grafts through respective first and second access sites on a first side of a pathological defect; advancing the grafts within delivery sheaths until each extends across the defect and is positioned within a common body passageway on a second side of the pathological defect; releasing the grafts from their respective delivery sheaths with the grafts opening in response to action of the shape memory alloy; and joining or attaching the grafts together within the common body passageway.

20 Claims, 24 Drawing Sheets

U.S. PATENT DOCUMENTS

| | | |
|---|---|---|
| 4,739,762 A | 4/1988 | Palmaz |
| 4,769,029 A | 9/1988 | Patel |
| 4,776,337 A | 10/1988 | Palmaz |
| 4,784,137 A | 11/1988 | Kulik et al. |
| 4,787,899 A | 11/1988 | Lazarus |
| 4,800,882 A | 1/1989 | Gianturco |
| 4,822,341 A | 4/1989 | Colone |
| 4,850,999 A | 7/1989 | Planck |
| 4,856,516 A | 8/1989 | Hillstead |
| 4,875,480 A | 10/1989 | Imbert |
| 4,886,062 A | 12/1989 | Wiktor |
| 4,907,336 A | 3/1990 | Gianturco |
| 4,913,141 A | 4/1990 | Hillstead |
| 4,925,445 A | 5/1990 | Sakamoto |
| 4,950,227 A | 8/1990 | Savin |
| 4,955,899 A | 9/1990 | Della Corna |
| 4,969,458 A | 11/1990 | Wiktor |
| 4,990,131 A | 2/1991 | Dardik |
| 4,990,151 A | 2/1991 | Wallsten |
| 4,990,155 A | 2/1991 | Wilkoff |
| 4,994,071 A | 2/1991 | MacGregor |
| 5,015,253 A | 5/1991 | MacGregor |
| 5,019,085 A | 5/1991 | Hillstead |
| 5,026,377 A | 6/1991 | Burton |
| 5,035,694 A | 7/1991 | Kasprzyk et al. |
| 5,035,706 A | 7/1991 | Gianturco |
| 5,041,126 A | 8/1991 | Gianturco |
| 5,045,072 A | 9/1991 | Castillo |
| 5,064,435 A | 11/1991 | Porter |
| 5,078,726 A | 1/1992 | Kreamer |
| 5,084,065 A | 1/1992 | Weldon |
| 5,100,422 A | 3/1992 | Berguer |
| 5,102,417 A | 4/1992 | Palmaz |
| 5,104,399 A | 4/1992 | Lazarus |
| 5,104,400 A | 4/1992 | Berguer |
| 5,104,404 A | 4/1992 | Wolff |
| 5,114,423 A | 5/1992 | Kasprzyk et al. |
| 5,116,365 A | 5/1992 | Hillstead |
| 5,122,154 A | 6/1992 | Rhodes |
| 5,123,917 A | 6/1992 | Lee |
| 5,131,908 A | 7/1992 | Dardik et al. |
| 5,133,732 A | 7/1992 | Wiktor |
| 5,135,536 A | 8/1992 | Hillstead |
| 5,151,105 A | 9/1992 | Kwan-Gett |
| 5,152,782 A | 10/1992 | Kowligi |
| 5,156,620 A | 10/1992 | Pigott |
| 5,159,920 A | 11/1992 | Cordon |
| 5,163,951 A | 11/1992 | Pinchuk |
| 5,163,958 A | 11/1992 | Pinchuk |
| 5,171,262 A | 12/1992 | MacGregor |
| 5,176,660 A | 1/1993 | Truckai |
| 5,178,618 A | 1/1993 | Kandarpa |
| 5,192,297 A | 3/1993 | Trescony et al. |
| 5,192,307 A | 3/1993 | Wall |
| 5,195,984 A | 3/1993 | Schatz |
| 5,207,695 A | 5/1993 | Trout, III |
| 5,211,658 A | 5/1993 | Clouse |
| 5,217,483 A | 6/1993 | Tower |
| 5,219,355 A | 6/1993 | Parodi |
| 5,222,971 A | 6/1993 | Willard et al. |
| 5,236,447 A | 8/1993 | Kubo |
| 5,246,445 A | 9/1993 | Yachia et al. |
| 5,246,452 A | 9/1993 | Sinnott |
| 5,254,107 A | 10/1993 | Soltesz |
| 5,258,021 A | 11/1993 | Duran |
| 5,258,027 A | 11/1993 | Berghaus |
| 5,266,073 A | 11/1993 | Wall |
| 5,275,622 A | 1/1994 | Lazarus et al. |
| 5,282,823 A | 2/1994 | Schwartz et al. |
| 5,282,824 A | 2/1994 | Gianturco |
| 5,282,847 A | 2/1994 | Trescony et al. |
| 5,282,860 A | 2/1994 | Matsuno |
| 5,290,305 A | 3/1994 | Inoue |
| 5,292,331 A | 3/1994 | Boneau |
| 5,304,197 A | 4/1994 | Pinchuk |
| 5,304,200 A | 4/1994 | Spaulding |
| 5,306,294 A | 4/1994 | Winston |
| 5,314,444 A | 5/1994 | Gianturco |
| 5,314,472 A | 5/1994 | Fontaine |
| 5,316,023 A | 5/1994 | Palmaz et al. |
| 5,318,535 A | 6/1994 | Miraki |
| 5,321,109 A | 6/1994 | Bosse |
| 5,330,490 A | 7/1994 | Wilk |
| 5,330,500 A | 7/1994 | Song |
| 5,330,528 A | 7/1994 | Lazim |
| 5,334,201 A | 8/1994 | Cowan |
| 5,334,301 A | 8/1994 | Heinke et al. |
| 5,342,387 A | 8/1994 | Summersq |
| 5,354,257 A | 10/1994 | Roubin et al. |
| 5,354,308 A | 10/1994 | Simon et al. |
| 5,358,493 A | 10/1994 | Schweich, Jr. et al. |
| 5,360,443 A | 11/1994 | Barone |
| 5,366,473 A | 11/1994 | Winston |
| 5,366,504 A | 11/1994 | Andersen et al. |
| 5,370,683 A | 12/1994 | Fontaine |
| 5,370,691 A | 12/1994 | Samson |
| 5,375,612 A | 12/1994 | Cottenceau et al. |
| 5,376,112 A | 12/1994 | Duran |
| 5,380,328 A | 1/1995 | Morgan |
| 5,382,261 A | 1/1995 | Palmaz |
| 5,383,892 A | 1/1995 | Cardon et al. |
| 5,383,927 A | 1/1995 | DeGoicoechea |
| 5,387,235 A | 2/1995 | Chuter |
| 5,389,106 A | 2/1995 | Tower |
| 5,395,390 A | 3/1995 | Simon et al. |
| 5,397,345 A | 3/1995 | Lazarus |
| 5,397,355 A | 3/1995 | Marin et al. |
| 5,403,341 A | 4/1995 | Solar |
| 5,405,322 A | 4/1995 | Lennox et al. |
| 5,405,377 A | 4/1995 | Cragg |
| 5,411,507 A | 5/1995 | Heckele |
| 5,411,549 A | 5/1995 | Peters |
| 5,417,708 A | 5/1995 | Hall et al. |
| 5,419,324 A | 5/1995 | Dillow |
| D359,802 S | 6/1995 | Fontaine |
| 5,421,955 A | 6/1995 | Lau et al. |
| 5,423,885 A | 6/1995 | Williams |
| 5,439,446 A | 8/1995 | Barry |
| 5,441,515 A | 8/1995 | Khosravi et al. |
| 5,441,516 A | 8/1995 | Wang et al. |
| 5,443,477 A | 8/1995 | Marin et al. |
| 5,443,496 A | 8/1995 | Schwartz et al. |
| 5,443,498 A | 8/1995 | Fontaine |
| 5,443,500 A | 8/1995 | Sigwart |
| 5,449,372 A | 9/1995 | Schmaltz et al. |
| 5,449,373 A | 9/1995 | Pinchasik et al. |
| 5,449,382 A | 9/1995 | Dayton |
| 5,453,090 A | 9/1995 | Martinez et al. |
| 5,453,235 A | 9/1995 | Calcote |
| 5,456,713 A | 10/1995 | Chuter |
| 5,466,509 A | 11/1995 | Kowligi |
| 5,468,138 A | 11/1995 | Bosse |
| 5,476,506 A | 12/1995 | Lunn |
| 5,480,423 A | 1/1996 | Ravenscroft |
| 5,484,444 A | 1/1996 | Braunchweiler |
| 5,489,295 A | 2/1996 | Piplani et al. |
| 5,496,364 A | 3/1996 | Schmitt |
| 5,496,365 A | 3/1996 | Fontaine et al. |
| 5,507,767 A | 4/1996 | Maeda et al. |
| 5,507,769 A | 4/1996 | Marin et al. |
| 5,507,771 A | 4/1996 | Gianturco |

| | | | | | |
|---|---|---|---|---|---|
| 5,507,995 A | 4/1996 | Schweich, Jr. et al. | 5,720,735 A | 2/1998 | Dorra |
| 5,512,229 A | 4/1996 | Bosse | 5,720,776 A | 2/1998 | Chuter et al. |
| 5,522,880 A | 6/1996 | Barone | 5,723,003 A | 3/1998 | Winston |
| 5,522,882 A | 6/1996 | Gaterud | 5,723,004 A | 3/1998 | Dereume et al. |
| 5,527,354 A | 6/1996 | Fontaine et al. | 5,725,534 A | 3/1998 | Rasmussen |
| 5,549,662 A | 8/1996 | Fordenbacher | 5,725,568 A | 3/1998 | Hastings |
| 5,549,663 A | 8/1996 | Cottone, Jr. | 5,725,570 A | 3/1998 | Heath |
| 5,562,698 A | 10/1996 | Parker | 5,728,065 A | 3/1998 | Follmer et al. |
| 5,562,724 A | 10/1996 | Vorwerk | 5,728,068 A | 3/1998 | Leone et al. |
| 5,562,726 A | 10/1996 | Chuter | 5,728,131 A | 3/1998 | Frantzen et al. |
| 5,569,295 A | 10/1996 | Lam | 5,733,328 A | 3/1998 | Fordenbacher |
| 5,571,170 A | 11/1996 | Palmaz et al. | 5,735,892 A | 4/1998 | Myers |
| 5,571,171 A | 11/1996 | Barone | 5,746,709 A | 5/1998 | Rom et al. |
| 5,571,173 A | 11/1996 | Parodi | 5,749,880 A | 5/1998 | Banas |
| 5,578,071 A | 11/1996 | Parodi | 5,749,920 A | 5/1998 | Quiachon et al. |
| 5,578,072 A | 11/1996 | Barone | 5,749,921 A | 5/1998 | Lenker et al. |
| 5,591,195 A * | 1/1997 | Tahari et al. ............... 623/1.13 | 5,752,966 A | 5/1998 | Chang |
| 5,591,196 A | 1/1997 | Marin et al. | 5,755,734 A | 5/1998 | Richter et al. |
| 5,591,197 A | 1/1997 | Orth et al. | 5,755,735 A | 5/1998 | Richter et al. |
| 5,591,228 A | 1/1997 | Edoga | 5,755,770 A | 5/1998 | Ravenscroft |
| 5,591,229 A | 1/1997 | Parodi | 5,755,771 A | 5/1998 | Penn et al. |
| 5,593,412 A | 1/1997 | Martinez et al. | 5,755,772 A | 5/1998 | Evans et al. |
| 5,607,444 A | 3/1997 | Lam | 5,755,773 A | 5/1998 | Evans et al. |
| 5,607,464 A | 3/1997 | Trescony et al. | 5,755,777 A | 5/1998 | Chuter |
| 5,609,624 A | 3/1997 | Kalis | 5,758,562 A | 6/1998 | Thompson |
| 5,609,625 A | 3/1997 | Piplani et al. | 5,760,006 A | 6/1998 | Shank |
| 5,609,627 A | 3/1997 | Goicoechea et al. | 5,766,201 A | 6/1998 | Ravenscroft et al. |
| 5,617,878 A | 4/1997 | Taheri | 5,769,882 A | 6/1998 | Fogarty et al. |
| 5,618,300 A | 4/1997 | Marin et al. | 5,769,885 A | 6/1998 | Quiachon et al. |
| 5,628,783 A | 5/1997 | Quiachon et al. | 5,776,180 A | 7/1998 | Goicoechea et al. |
| 5,628,786 A | 5/1997 | Banas | 5,782,765 A | 7/1998 | Jonkman |
| 5,628,788 A | 5/1997 | Pinchuk | 5,782,906 A | 7/1998 | Marshall et al. |
| 5,632,763 A | 5/1997 | Glastra | 5,782,909 A | 7/1998 | Quiachon et al. |
| 5,632,778 A | 5/1997 | Goldstein | 5,788,626 A | 8/1998 | Thompson |
| 5,639,278 A | 6/1997 | Dereume et al. | 5,797,953 A | 8/1998 | Tekulve |
| 5,641,443 A | 6/1997 | Cacpte | 5,800,456 A | 9/1998 | Maeda et al. |
| 5,643,312 A | 7/1997 | Fischell et al. | 5,800,508 A | 9/1998 | Goicoechea et al. |
| 5,645,559 A | 7/1997 | Hachtman | 5,800,516 A | 9/1998 | Fine et al. |
| 5,649,952 A | 7/1997 | Lam | 5,800,518 A | 9/1998 | Piplani et al. |
| 5,653,743 A | 8/1997 | Martin | 5,800,520 A | 9/1998 | Fogarty et al. |
| 5,653,745 A | 8/1997 | Trescony et al. | 5,810,870 A | 9/1998 | Myers |
| 5,653,747 A | 8/1997 | Dereume et al. | 5,824,036 A | 10/1998 | Lauterjung |
| 5,662,700 A | 9/1997 | Lazarus | 5,824,037 A | 10/1998 | Fogarty et al. |
| 5,662,703 A | 9/1997 | Yurek et al. | 5,824,039 A | 10/1998 | Piplani et al. |
| 5,667,523 A | 9/1997 | Bynon | 5,824,040 A | 10/1998 | Cox et al. |
| 5,669,924 A | 9/1997 | Shaknovich | 5,824,041 A | 10/1998 | Lenker et al. |
| 5,669,936 A | 9/1997 | Lazarus | 5,824,042 A | 10/1998 | Lombardi et al. |
| 5,674,241 A | 10/1997 | Bley | 5,824,043 A | 10/1998 | Cottone, Jr. |
| 5,674,276 A | 10/1997 | Andersen et al. | 5,824,044 A | 10/1998 | Yazici et al. |
| 5,676,696 A | 10/1997 | Marcade | 5,824,046 A | 10/1998 | Smith |
| 5,676,697 A | 10/1997 | McDonald | 5,824,054 A | 10/1998 | Khosravi |
| 5,681,345 A | 10/1997 | Euteneuer | 5,824,055 A | 10/1998 | Liozzi et al. |
| 5,681,346 A | 10/1997 | Orth et al. | 5,827,310 A | 10/1998 | Marin et al. |
| 5,683,448 A | 11/1997 | Cragg | 5,827,320 A | 10/1998 | Richter et al. |
| 5,683,449 A | 11/1997 | Marcade | 5,827,327 A | 10/1998 | McHaney |
| 5,683,450 A | 11/1997 | Goicoechea et al. | 5,830,229 A | 11/1998 | Konya et al. |
| 5,683,451 A | 11/1997 | Lenker et al. | 5,833,651 A | 11/1998 | Donovan et al. |
| 5,685,847 A | 11/1997 | Barry | 5,840,011 A | 11/1998 | Landgrebe et al. |
| 5,693,083 A | 12/1997 | Baker et al. | 5,843,031 A | 12/1998 | Hermann et al. |
| 5,693,084 A | 12/1997 | Chuter | 5,843,120 A | 12/1998 | Israel |
| 5,693,085 A | 12/1997 | Limon et al. | 5,843,158 A | 12/1998 | Lenker et al. |
| 5,693,086 A | 12/1997 | Goicoechea et al. | 5,843,160 A | 12/1998 | Rhodes |
| 5,695,517 A | 12/1997 | Marin et al. | 5,855,598 A | 1/1999 | Pinchuk |
| 5,697,948 A | 12/1997 | Marin et al. | 5,857,998 A | 1/1999 | Barry |
| 5,697,971 A | 12/1997 | Fischell et al. | 5,858,556 A | 1/1999 | Eckert |
| 5,700,285 A | 12/1997 | Myers | 5,860,998 A | 1/1999 | Robinson et al. |
| 5,702,418 A | 12/1997 | Ravenscroft | 5,861,027 A | 1/1999 | Trapp |
| 5,713,917 A | 2/1998 | Leonhardt et al. | 5,868,777 A | 2/1999 | Lam |
| 5,716,365 A | 2/1998 | Goicoechea et al. | 5,871,537 A | 2/1999 | Holman et al. |
| 5,718,159 A | 2/1998 | Thompson | 5,871,538 A | 2/1999 | Dereume |
| 5,718,724 A | 2/1998 | Goicoechea et al. | 5,876,397 A | 3/1999 | Edelman et al. |

| | | |
|---|---|---|
| 5,893,868 A | 4/1999 | Hanson et al. |
| 5,893,887 A | 4/1999 | Jayaraman |
| 5,899,890 A | 5/1999 | Chiang et al. |
| 5,902,308 A | 5/1999 | Murphy |
| 5,904,713 A | 5/1999 | Leschinsky |
| 5,906,619 A | 5/1999 | Olson et al. |
| 5,906,640 A | 5/1999 | Penn et al. |
| 5,906,641 A | 5/1999 | Thompson et al. |
| 5,908,448 A | 6/1999 | Roberts et al. |
| 5,916,263 A | 6/1999 | Goicoechea et al. |
| 5,916,264 A | 6/1999 | Von Oepen |
| 5,919,224 A | 7/1999 | Thompson et al. |
| 5,928,260 A | 7/1999 | Chin et al. |
| 5,935,667 A | 8/1999 | Calcote |
| 5,938,696 A | 8/1999 | Goicoechea et al. |
| 5,944,726 A | 8/1999 | Blaeser et al. |
| 5,944,750 A | 8/1999 | Tanner et al. |
| 5,951,599 A | 9/1999 | McCrory |
| 5,954,693 A | 9/1999 | Barry |
| 5,957,973 A | 9/1999 | Quiachon et al. |
| 5,957,974 A | 9/1999 | Thompson et al. |
| 5,961,548 A | 10/1999 | Shmulewitz |
| 5,968,069 A | 10/1999 | Dusbabek et al. |
| 5,968,088 A | 10/1999 | Hansen et al. |
| 5,980,565 A | 11/1999 | Jayaraman |
| 5,993,481 A * | 11/1999 | Marcade et al. ............ 623/1.13 |
| 6,007,543 A | 12/1999 | Ellis et al. |
| 6,015,431 A | 1/2000 | Thornton et al. |
| 6,015,432 A | 1/2000 | Rakos et al. |
| 6,016,810 A | 1/2000 | Ravenscroft |
| 6,017,363 A | 1/2000 | Hojeibane |
| 6,017,364 A | 1/2000 | Lazarus |
| 6,019,778 A | 2/2000 | Wilson et al. |
| 6,019,786 A | 2/2000 | Thompson |
| 6,024,763 A | 2/2000 | Lenker et al. |
| 6,027,526 A | 2/2000 | Limon et al. |
| 6,027,529 A | 2/2000 | Roychowdhury et al. |
| 6,030,413 A | 2/2000 | Lazarus |
| 6,030,415 A | 2/2000 | Chuter |
| 6,033,435 A | 3/2000 | Penn et al. |
| 6,036,697 A | 3/2000 | DiCaprio |
| 6,036,723 A | 3/2000 | Anidjar et al. |
| 6,036,725 A | 3/2000 | Avellanet |
| 6,039,749 A | 3/2000 | Marin et al. |
| 6,039,758 A | 3/2000 | Quiachon et al. |
| 6,048,356 A | 4/2000 | Ravenscroft et al. |
| 6,051,020 A | 4/2000 | Goicoechea et al. |
| 6,056,775 A | 5/2000 | Borghi et al. |
| 6,059,821 A | 5/2000 | Anidjar et al. |
| 6,059,823 A | 5/2000 | Holman et al. |
| 6,059,824 A | 5/2000 | Taheri |
| 6,063,111 A | 5/2000 | Hieshima et al. |
| 6,068,655 A | 5/2000 | Seguin et al. |
| 6,070,589 A | 6/2000 | Keith et al. |
| 6,077,273 A | 6/2000 | Euteneuer et al. |
| 6,078,832 A | 6/2000 | Lenker et al. |
| 6,086,577 A | 7/2000 | Ken et al. |
| 6,086,611 A | 7/2000 | Duffy et al. |
| 6,090,127 A | 7/2000 | Globerman |
| 6,090,128 A | 7/2000 | Douglas |
| 6,090,133 A | 7/2000 | Richter et al. |
| 6,093,199 A | 7/2000 | Brown et al. |
| 6,097,978 A | 8/2000 | Demarais et al. |
| 6,099,558 A | 8/2000 | White et al. |
| 6,099,560 A | 8/2000 | Penn et al. |
| 6,102,938 A | 8/2000 | Evans et al. |
| 6,102,942 A | 8/2000 | Ahari |
| 6,110,191 A | 8/2000 | Dehdashtian et al. |
| 6,110,198 A | 8/2000 | Fogarty et al. |
| 6,117,117 A | 9/2000 | Mauch |
| 6,117,156 A | 9/2000 | Richter et al. |
| 6,117,157 A | 9/2000 | Tekulve |
| 6,117,167 A | 9/2000 | Goicoechea et al. |
| 6,123,722 A | 9/2000 | Fogarty et al. |
| 6,126,685 A | 10/2000 | Lenker et al. |
| 6,129,754 A | 10/2000 | Hanson et al. |
| 6,132,450 A | 10/2000 | Hanson et al. |
| 6,132,459 A | 10/2000 | Piplani et al. |
| 6,302,906 B1 | 10/2001 | Goicoechea et al. |

FOREIGN PATENT DOCUMENTS

| | | |
|---|---|---|
| EP | 0657147 A2 | 10/1994 |
| EP | 0686379 B1 | 12/1995 |
| EP | 734698 A2 | 10/1996 |
| EP | 783873 A2 | 7/1997 |
| EP | 800801 A1 | 10/1997 |
| EP | 830853 A1 | 3/1998 |
| EP | 832616 A1 | 4/1998 |
| EP | 0855170 A2 | 7/1998 |
| EP | 880948 A1 | 12/1998 |
| EP | 0928606 A1 | 7/1999 |
| EP | 937442 A2 | 8/1999 |
| EP | 0947179 A2 | 10/1999 |
| EP | 1000590 A1 | 5/2000 |
| FR | 0 566 807 A1 | 10/1993 |
| FR | 2733682 A1 | 11/1996 |
| FR | 2740346 A1 | 4/1997 |
| FR | 2743293 A1 | 7/1997 |
| GB | 0 662 307 A2 | 9/1948 |
| GB | 1 205 743 | 9/1970 |
| JP | 5524095 A | 2/1980 |
| JP | 60220030 A | 11/1985 |
| JP | 62231657 A | 3/1988 |
| JP | 464367 A | 2/1992 |
| JP | 4263852 A | 4/1992 |
| JP | 5 76603 A | 3/1993 |
| JP | 5 269199 A | 10/1993 |
| JP | 7529 A | 10/1994 |
| JP | 6282730 A | 10/1994 |
| JP | 7 24072 A | 1/1995 |
| JP | 7100210 A | 4/1995 |
| JP | 6 86827 A | 6/1998 |
| SU | 1680055 | 5/1988 |
| WO | 8704935 A1 | 8/1987 |
| WO | 9516406 A1 | 6/1995 |
| WO | 9521592 A1 | 8/1995 |
| WO | 9626689 A1 | 9/1996 |
| WO | 96/34580 A1 | 11/1996 |
| WO | 9724081 A1 | 7/1997 |
| WO | 9725000 A1 | 7/1997 |
| WO | 9733532 A2 | 9/1997 |
| WO | 9807389 A1 | 2/1998 |
| WO | 98/19628 A1 | 5/1998 |
| WO | 9823322 A1 | 6/1998 |
| WO | 9836709 A1 | 8/1998 |
| WO | 9853761 A1 | 12/1998 |
| WO | 9908744 A1 | 2/1999 |
| WO | 9911199 A1 | 3/1999 |

* cited by examiner

FIG. 4
FIG. 8
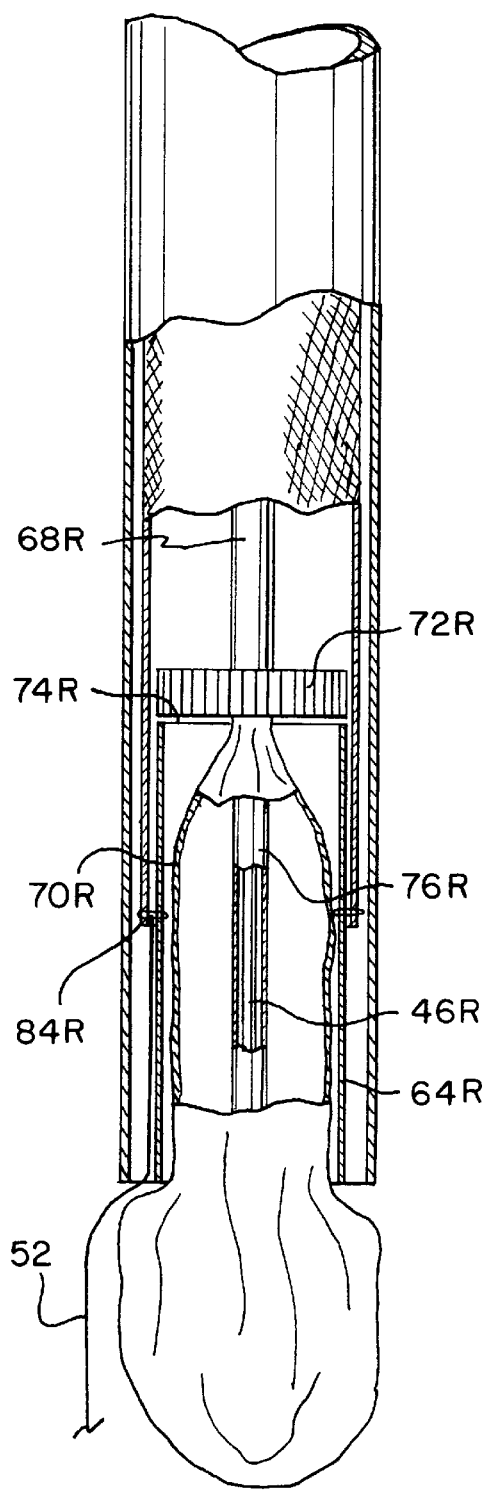
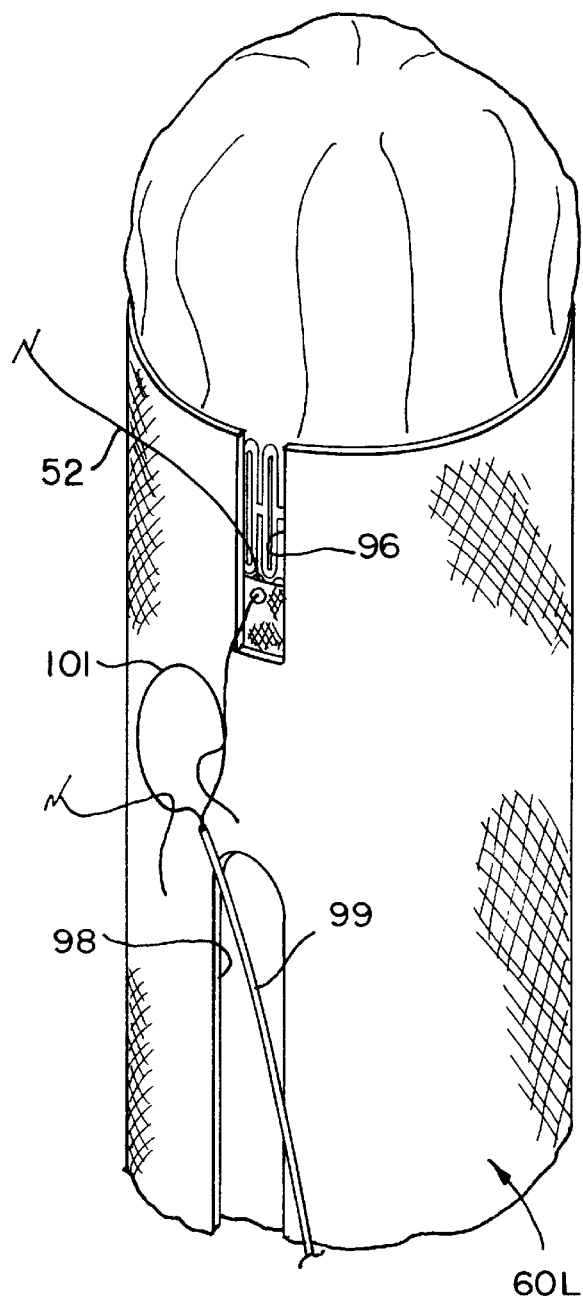

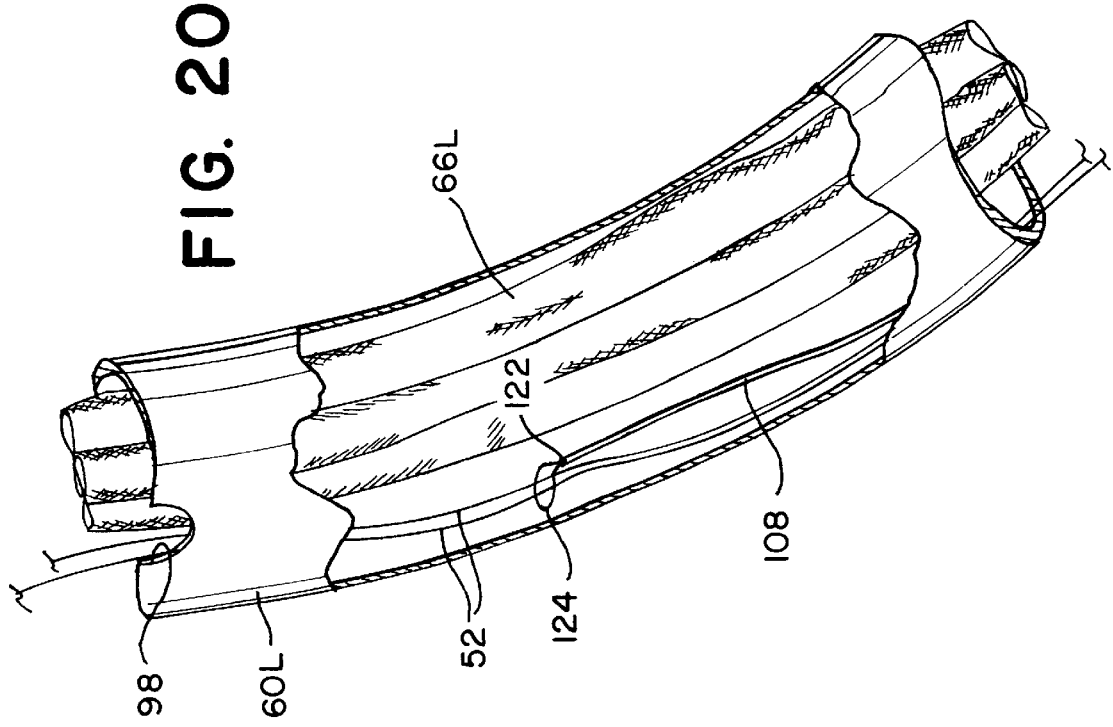
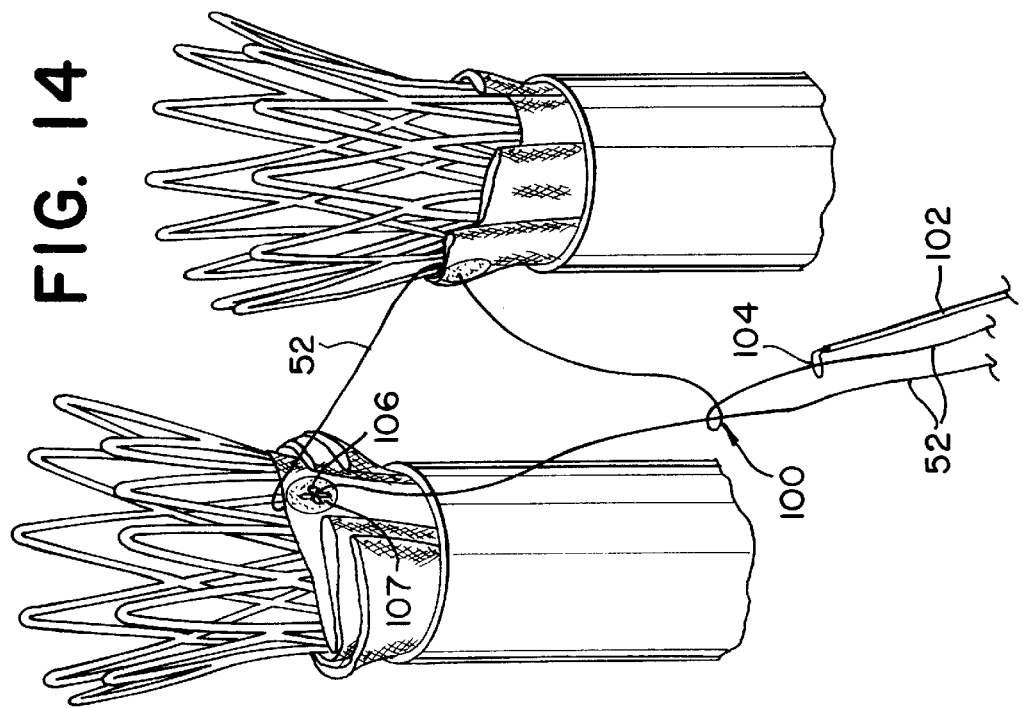

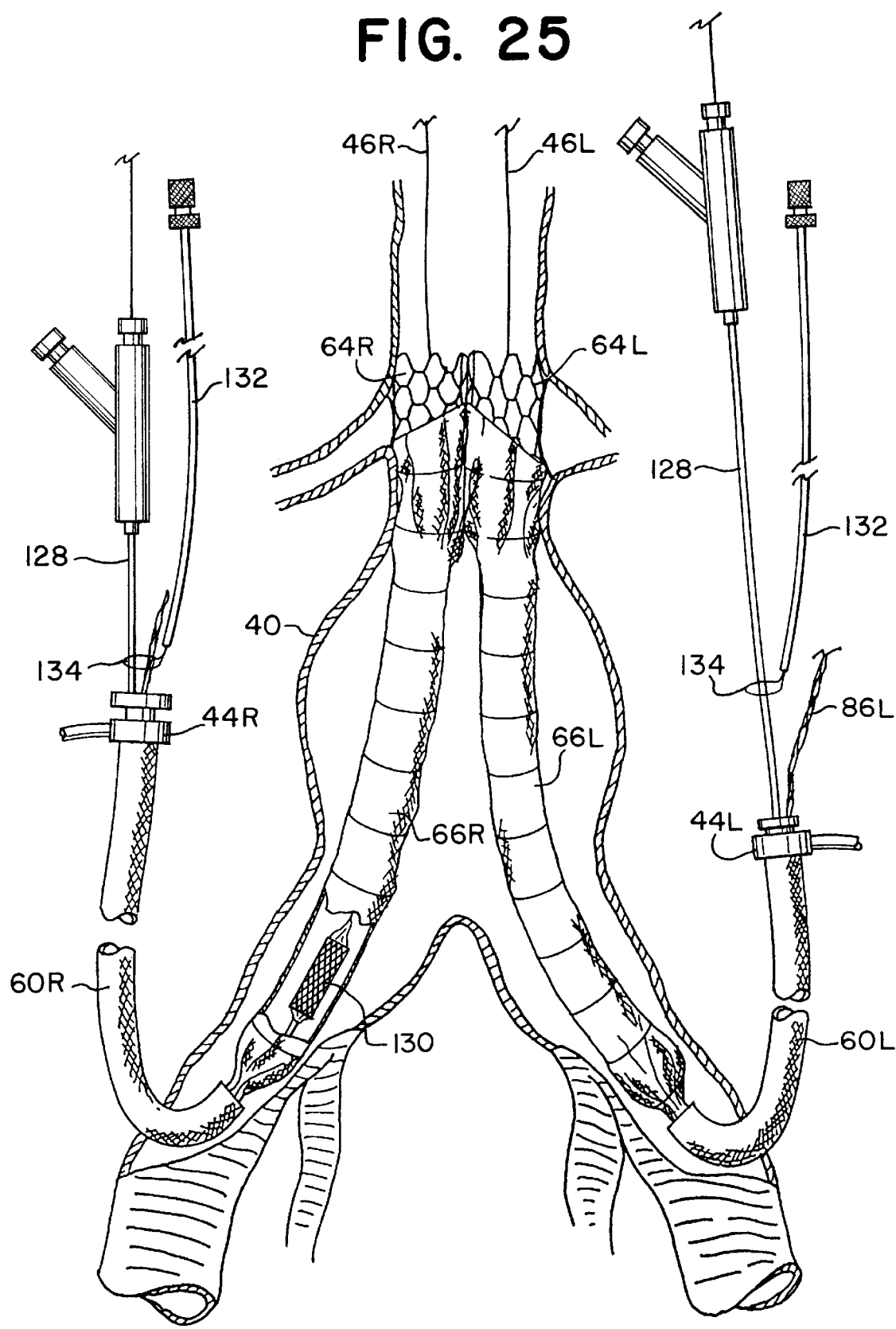

METHOD FOR JOINING GRAFTS IN A COMMON BODY PASSAGEWAY

This application is a continuation of U.S. patent application Ser. No. 08/904,977, filed on Aug. 1, 1997, now U.S. Pat. No. 6,070,589 issued Jun. 6, 2000.

FIELD OF THE INVENTION

This invention relates to an apparatus and method for endoluminally deploying a graft in a body passageway, for example, for the purpose of isolating an abdominal aortic aneurysm in the vicinity of a branching portion of vasculature.

BACKGROUND OF THE INVENTION

Marin et al. U.S. Pat. No. 5,507,769 describes a method and apparatus for endoluminally deploying a graft across an aortic aneurysm and associated common iliac aneurysms. In that patent, separate grafts are advanced through a patient's femoral and iliac arteries and aligned in a common region in the aorta above the aneurysm. Cephalic stents are deployed in that region to effectively create a bifurcated graft with the individual legs of the graft extending into the patient's arteries. Suitable stents are likewise deployed in these legs caudal of the aneurysm, thus isolating the aneurysm. See also Palmaz et al. U.S. Pat. Nos. 5,316,023 and 5,571,170.

Marin et al. U.S. Pat. No. 5,507,769, which issued Apr. 16, 1996, Palmaz et al. U.S. Pat. No. 5,316,023, which issued May 31, 1994, and Palmaz et al. U.S. Pat. No. 5,571,170, which issued Nov. 5, 1996, in their entireties are hereby incorporated by reference.

One problem that must be contended with when deploying separate grafts for alignment in a common region of a patient's vasculature is ensuring that a pathological defect has been effectively isolated because failure to do so may result in complications to the patient. There exists a need in the art for an apparatus and method for bypassing and effectively isolating a pathological defect, such as an abdominal aortic aneurysm, and an object of the invention is to satisfy that need and provide other advantages as set forth in the following description.

SUMMARY OF THE INVENTION

These and other needs are addressed, according to one aspect of the invention, by a method for endoluminally excluding a pathological defect in the vicinity of a branching passageway within a patient, such as an infrarenal aortic aneurysm. The method comprises the steps of introducing first and second graftstents through respective first and second access sites on one side of the pathological defect. The first and second graftstents are advanced until each extends across the pathological defect and is positioned in a common body passageway. The graftstents are joined together on the other side of the pathological defect within the common body passageway. The joining step may comprise tying the first and second graftstents together. When the pathological defect, e.g., an aneurysm, is in the aortic artery, the graftstents are advanced through the femoral and iliac arterial system and secured in a common region above the aneurysm. Of course, the method may be performed in passageways other than those that form the arterial system, and may be performed by advancing the graftstent from a common passageway to a branched passageway. When the inventive method is performed in the vascular system, the deployed vascular stents are preferably shaped in a noncircular configuration when expanded, for example, in a generally "D" shaped configuration and may be expanded simultaneously, as described in U.S. Pat. No. 5,507,769 for METHOD AND APPARATUS FOR FORMING AN ENDOLUMINAL BIFURCATED GRAFT, issued Apr. 16, 1996, the entirety of which is hereby incorporated by reference as if set forth herein. The deployed stents preferably hemostatically seal the graftstents to the common vessel wall and to each other so that blood is excluded from the aneurysmal cavity. One advantage of this system is the ability to use smaller delivery catheters in each vascular branch rather than one larger catheter sized to deploy a graft which is sufficiently large to bypass the aorta.

According to yet another aspect of the present invention, a graftstent for hemostatically bypassing an aneurysm is provided. The graftstent comprises a segment of graft material having serially spaced support hoops, for example, made of nitinol, a nitinol or self-expanding stent, and an elongated line or tab (attached to the end opposite the stent) that extends from the patient so that tension applied to the line or tab from outside the patient positions one end of the graftstent relative to the other. The segment of graft material connects at one end to a balloon-expandable stent and at another end to the self-expanding stent. The graftstent may have the segment of graft material cut on a bias, as noted above.

According to still another aspect of the invention, left and right graftstents are aligned and anchored in situ by advancing a knot or anchor bead from a location external to the patient to the site where the left and right graftstents have been advanced. In the case of an anchor bead, the bead is provided with a plurality of funnel-like seal rings which provide little resistance to movement in a first direction yet great resistance to movement in a second, opposite direction. The anchor bead can be advanced over an anchor line threaded through the left and right grafts to draw the graftstents together. Once drawn together, the knot or anchor bead junction prevents the graftstents from separating, and ensures alignment of both graftstents to each other, both rotational and longitudinal, thereby assuring proper deployment of both graftstents and exclusion of the aneurysm.

According to a further aspect of the invention, a graftstent system is disclosed which comprises a first graftstent, a second graftstent, and an endoluminal connector. The connector has a first portion that attaches to the first graftstent and a second portion that attaches to the second graftstent. The connector is adjustable to endoluminally join the first and second graftstents.

These and other objects, features and advantages of the present invention will be readily apparent from the following detailed description of the invention taken in conjunction with the accompanying drawings.

BRIEF DESCRIPTION OF THE DRAWINGS

FIG. 4 is a detail view, partially in section, of a first delivery sheath in accordance with another aspect of the present invention;

FIG. 8 is a detail view of the second delivery sheath showing the threading of the anchor line through the second graftstent;

FIG. 14 is a detail view, with the graftstents shown partially withdrawn from their delivery sheaths, illustrating the advancement of the knot using a pusher;

FIG. 20 is a detail view of the cutting wire positioned over the anchor lines and further showing the left graftstent in a folded state;

FIG. 25 is the same view as FIG. 23 at a further stage of the method of the present invention wherein a graft cutter is being advanced over the stent delivery catheter and a tab extending from a caudal end of each graft;

DETAILED DESCRIPTION OF THE INVENTION

Figure 1:
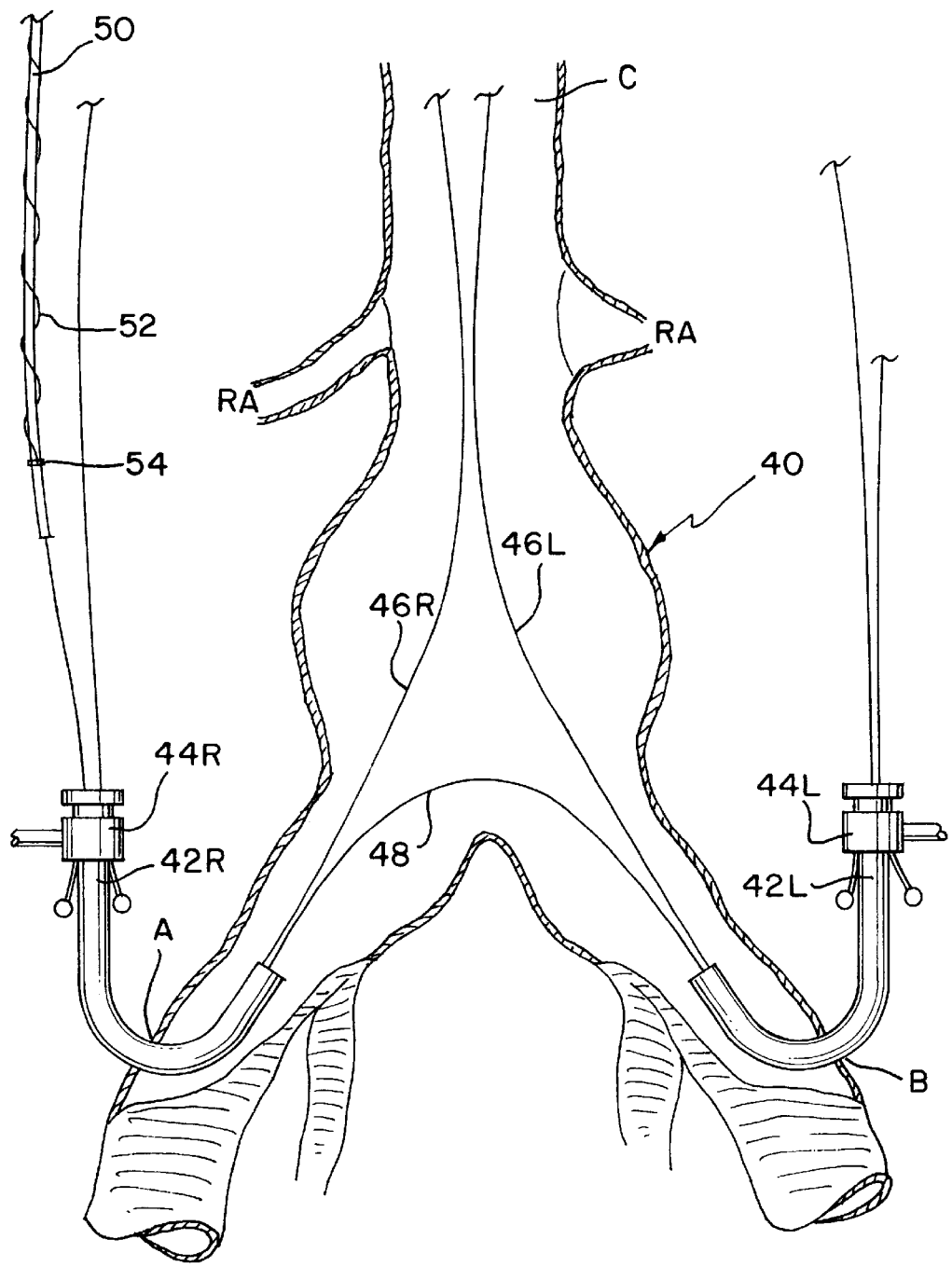
FIG. 1 is a diagrammatic view of a portion of a human vascular system depicting an abdominal aortic aneurysm in accordance with one stage of the method of the present invention wherein aortic guidewires have been introduced through introducers inserted at each of a right and left vascular branch and wherein a bifurcation guidewire has been threaded from the right branch to the left branch.

The present invention was developed as an improvement over the endoluminal grafting procedure disclosed in U.S. Pat. No. 5,507,769 but the invention is not limited to that procedure. Just as in the case of U.S. Pat. No. 5,507,769, the invention may be used to bypass pathological defects other than aneurysms and vascular occlusions, for example malignancies. The invention is not limited to arteries or even the vascular system, and will have utility in other body passageways, such as the trachea, esophagus or colon, or wherever grafts have or may have utility. Nevertheless, despite the broad application of the basic principles of the invention, the preferred embodiment is described below in connection with the placement of a bifurcated graft for the purpose of bypassing an aortic aneurysm encompassing the junction of the aorta and the iliac arteries.

In the following description and claims, the terms used have the definitions set forth in U.S. Pat. No. 5,507,769. Specifically, the terms "distal" and "proximal" refer to the devices themselves, and not to the vasculature, with the portion of the device remaining outside being the proximal end and the other end being the distal end. The vasculature is referred to with respect to the cephalic (closer to head) and caudal (further from head) directions. The term "above" refers to the regions cephalic of the aneurysm (for example) and "below" refers to the region of the vasculature caudal of the aneurysm.

In the Figures, elements introduced through the left branch of the patient's vasculature (the right side of the Figures) have an "L" designation after their respective reference numerals and elements in the right branch have an "R" designation, and such elements are more generally referred to throughout this specification without such branch designations when there exists bilateral symmetry. It should be understood, however, that such designations are arbitrary, are merely for simplifying the following discussion, and that devices introduced and the steps performed at the left branch in the following description could readily be introduced and performed at the right branch, and vice versa.

By way of overview and introduction, the present invention provides a method and apparatus particularly suited for treating aortic aneurysms which extend to the aortoiliac junction in which there is insufficient healthy tissue at the junction of the aorta and the iliac arteries to seat a stent. By seating, it is meant that the graft is implanted, fixed or otherwise attached to the vasculature. The present method and apparatus provide separate grafts to the aorta through each branch of the iliac arterial system. These grafts are unified to form a new, double barrel, bifurcated graft, which in this detailed illustration, is in the vicinity of the renal arteries to effectively isolate an infrarenal aortic aneurysm.

FIG. 1 depicts an aneurysm 40 located in the infrarenal aorta, that is, in the portion of the aorta disposed caudal of the left and right renal arteries RA, which extends to the aortoiliac junction. This anatomical condition precludes securing a simple tubular graftstent to the caudal end of the aorta. Each common iliac artery further branches into the internal (not shown) and external iliac arteries. The external iliac artery becomes the femoral artery below the inguinal ligament (not shown). In conventional manner, the femoral artery of each branch is accessed from the patient's thighs by an arterial incision where the vessel is close to the undersurface of the skin.

As a first step in the present method, as is conventional in many endovascular procedures, an introducer 42 comprising a tubular sheath is introduced into the patient's vasculature to permit insertion of the catheters, wires and instruments necessary to bypass the aneurysm. In the illustrated preferred embodiment, introducer 42 is a peel-away type introducer. Hemostatic valve 44 is either splittable along with the peel-away introducer 42, or is removable and large enough in diameter to slide over other devices such as the delivery sheath 60, described below. As shown, an introducer 42R has been inserted into the right femoral artery and an introducer 42L has been inserted into the left femoral artery (the left branch). The upward orientation of the introducers 42 is for ease of illustration only. Each introducer 42 is preferably 8 to 10 French in diameter and includes a hemostatic valve 44 (e.g., a Tuohy-Borst valve) at its proximal end to minimize backbleed prior to insertion of the graftstent delivery sheaths 60, described below. The hemostatic valve is arranged so that the introducer can be peeled away, and preferably is physically separable from the introducer 42.

With the introducer sheaths 42 in place and the valves 44 at least partially open, aortic guidewires 46R,46L are introduced into the right (ipsilateral) and left (contralateral) vascular branches, respectively, at each groin through incision points A and B in conventional manner. These incisions expose the common femoral arteries on the right and left sides, respectively. The guidewires 46 are separately advanced until their distal ends are well above the aneurysm within the vasculature (point C). The guidewires 46 are at least 0.025 inches in diameter, and preferably is 0.032 to 0.035 inches or more, and have a length of approximately 180 cm. The guidewires may be made of stainless steel and are conventionally covered with a synthetic material, such as TEFLON. The guidewires 46 may remain in a fixed position throughout the endoluminal bypass procedure. In addition, a bifurcation wire 48 is introduced through one of the introducers 42R, 42L to a location within the aneurysmal sac 40. This guidewire may made of the same materials as the aortic guidewire, although it need only be about 0.014 to about 0.018 inches in diameter and about 100 cm long. A snare catheter (not shown) is advanced through the other introducer and manipulated until the bifurcation wire 48 is within the snare of the snare catheter. The snare is then engaged and the bifurcation wire 48 drawn out through the introducer in which the snare catheter was introduced. For example, if the bifurcation wire 48 was introduced through the right branch, then the snare catheter would be introduced through the left branch and the distal end of the bifurcation wire 48 would be drawn through the left branch to a location external of the patient.

As a result, the bifurcation wire 48 is installed over and across the bifurcation, with its ends external to the patient extending from the right and left introducers 42R, 42L. The valves 44 may be temporarily closed to minimize backbleed until the operator is ready to proceed. The aortic guidewires 46 may be introduced before or after the bifurcation wire 48 is positioned.

Figure 2:
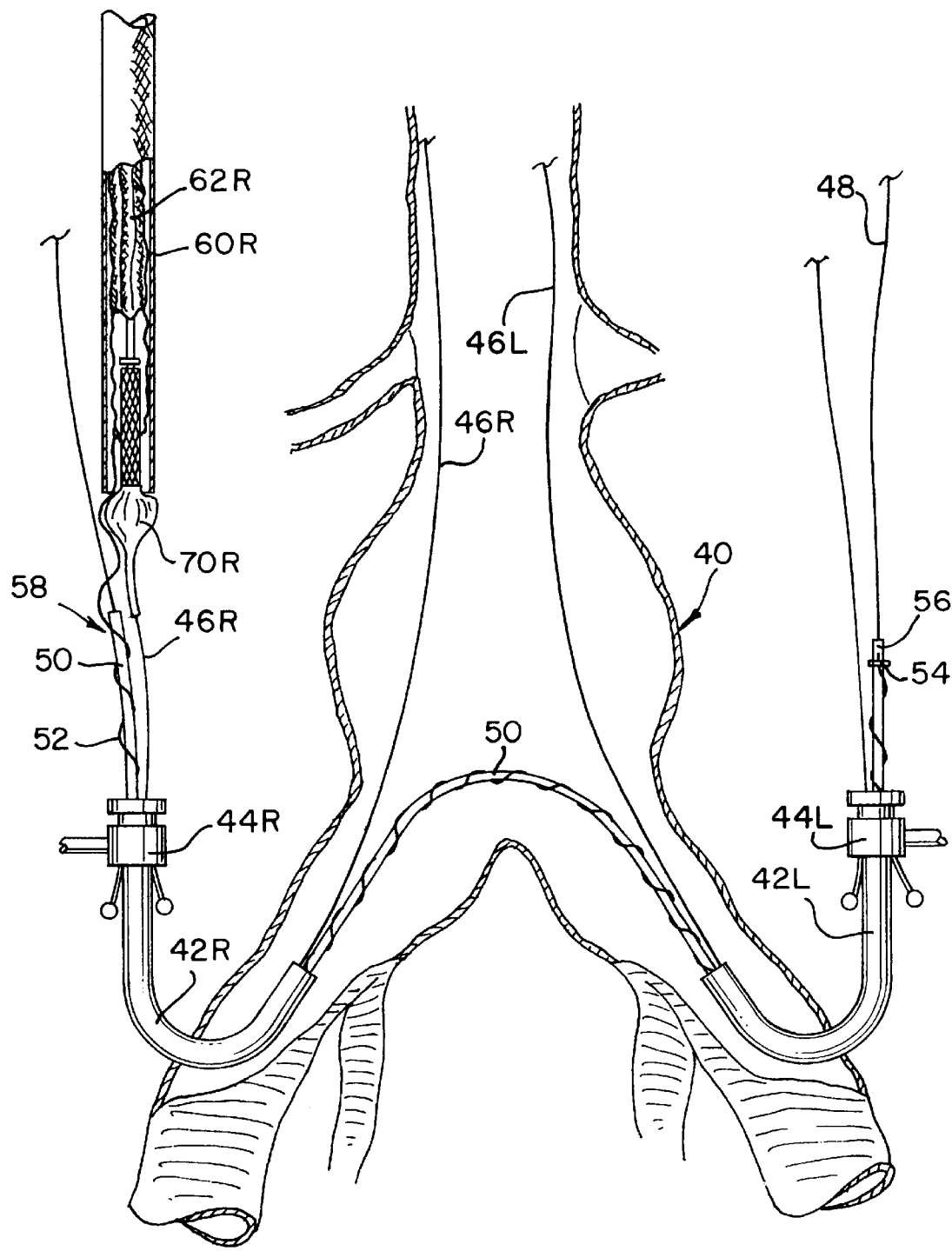
FIG. 2 is the same view as FIG. 1 at a further stage of the method of the present invention wherein an anchor catheter has been threaded over the bifurcation guidewire from the right branch to the left branch.

As shown in FIG. 2, a suture or anchor line catheter 50 next is advanced over one end of the bifurcation wire 48. The anchor line catheter 50 includes one or more suture or anchor lines 52 that are preferably spirally wrapped about the anchor line catheter 50 and have an overall length of 120 cm. The anchor lines may be made of any conventional high strength suture material, and preferably are made of a monofilament material to facilitate knot advancement and/or advancement of an anchor bead, described below. One end of the anchor lines 52 is secured to the anchor line catheter 50 by a restraint 54. The other end of the anchor lines 52 are attached to a first graftstent 62R, as perhaps better seen in the views of FIGS. 14, 17–18, for example. FIG. 2 shows the anchor line catheter 50 at a further stage of advancement, with each end of the catheter extending from a respective introducer 42R, 42L. Specifically, the distal end 56 of the anchor line catheter 50 is shown extending from the left introducer (42L) and the proximal end 58 is shown extending from the right introducer (42R).

Figure 3:
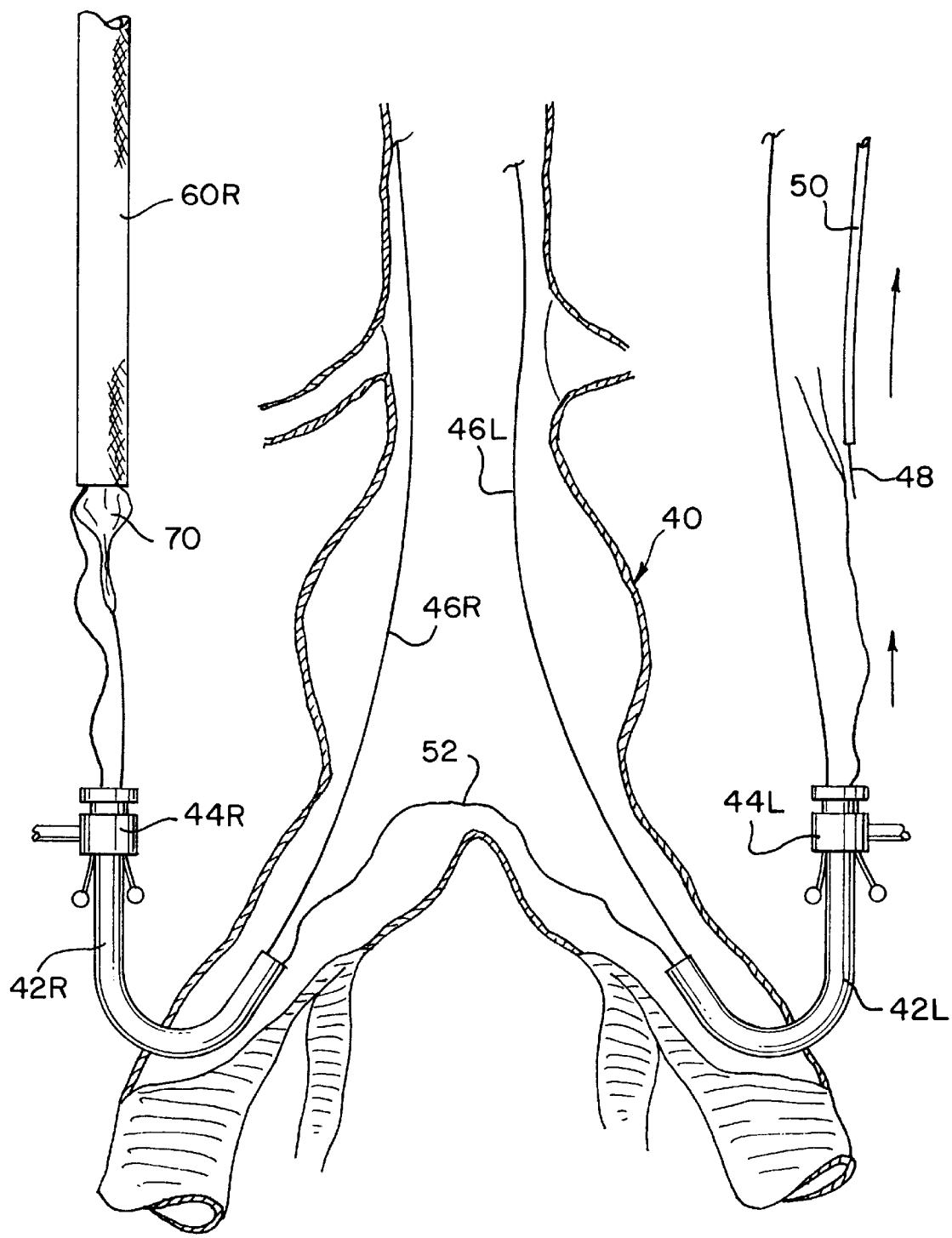
FIG. 3 is the same view as FIG. 2 at a further stage of the method of the present invention wherein the anchor catheter and bifurcation guidewire have been withdrawn from the patient leaving behind an anchor line which extends from the right branch to the left branch.

With the anchor line now extending out of the left branch, the anchor catheter 50 and the bifurcation wire 48 may be withdrawn from the patient leaving behind the anchor line 52 extending across the aneurysmal sac 40 between the right and left branches (see FIG. 3).

An alternative technique for passing the anchor lines 52 from the right femoral artery to the left femoral artery is to attach the proximal ends 82 of the anchor lines 52 directly to the exposed end of the bifurcation guidewire 48. The bifurcation guidewire 48 is then withdrawn from the introducer sheath 42L which pulls the anchor lines 52 with it. This approach eliminates the need for the anchor line catheter 50. Once the anchor lines 52 emerge out of the introducer sheath 42L, the ends 82 are detached from the bifurcation guidewire 48 and the bifurcation guidewire 48 is removed.

Figure 24:
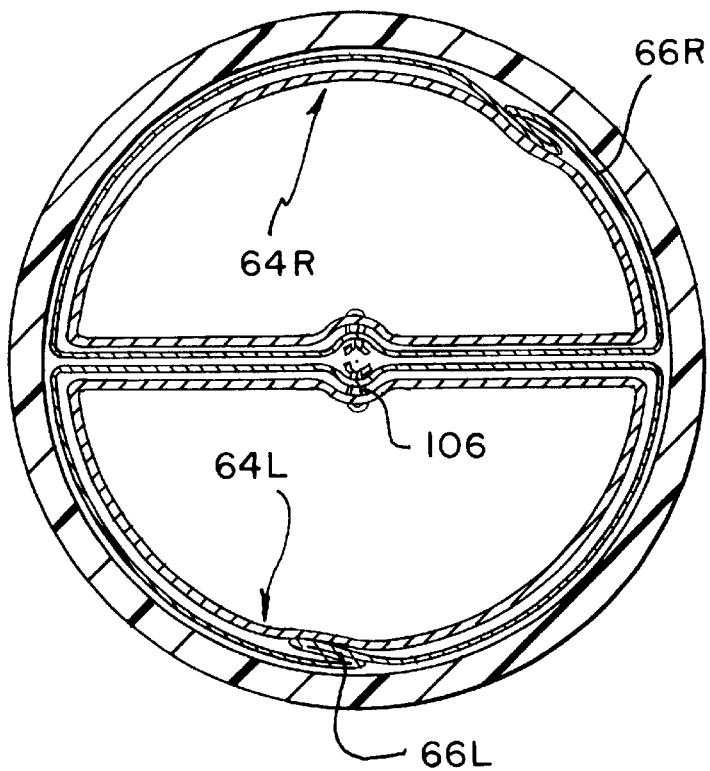
FIG. 24 is a cross-sectional view taken along lines 24—24 of FIG. 23.

With further reference to FIGS. 24, a first delivery sheath 60R is shown having the anchor wires 52 extending into its distal end. The delivery sheath 60 is preferably a thin-wall TEFLON sheath approximately 40 cm long and having a 12 to 18 French diameter. To add column strength or kink resistance, the walls of the sheath 60 may include reinforcing, for example, stainless-steel or fiber braiding. The delivery sheath 60R houses a first graftstent 62R which comprises an aortic stent 64 pre-attached at three to about eight sites to a folded, packed graft 66R, described in more detail below. In addition, the delivery sheath 60R houses a lead balloon catheter 68R having an inflatable balloon 70R partially housed within the delivery sheath 60R, concentric with the aortic stent 64R, and partially extending from the distal end thereof with a gradual cone angle for smooth introduction into the patient. The balloon may be of conventional material, for example, PET, Nylon or PEBAX, and may include several layers of the same or different material, although a thin wall, low-profile is preferred. Overall, the balloon may be about 5 cm in length and expand to about 5 to about 7 mm in diameter. The lead balloon catheter also has a ledge 72R positioned to abut the proximal edge 74R of the aortic stent 64R to restrain proximal motion of the stent 64R when the delivery sheath 60R is retracted relative to the lead balloon catheter 68R. The lead balloon catheter 68R has a lumen 76R which is sized to receive the aortic guidewire 46R and is threaded over aortic guidewire 46R, as seen in FIGS. 2 and 3.

Figure 18:
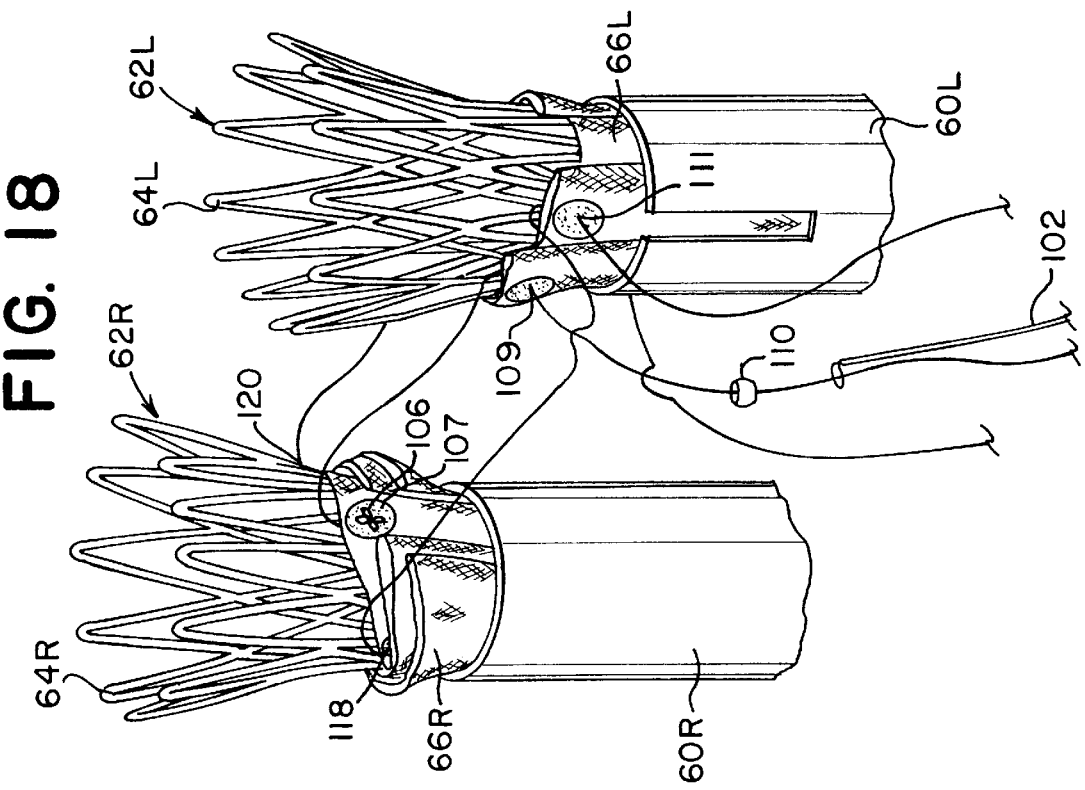
FIG. 18 is a similar view to that of FIG. 17 wherein plural anchor lines are provided for securing the first and second graftstents together at multiple locations.

The anchor lines 52 extend through the distal end of the delivery sheath 60R to one or more attachment points on the graftstent 62R, and in the preferred embodiment, to one or more attachment points on the graft 66R (see, for example, FIGS. 4 and 18). In many of the drawings, the anchor lines 52, if there are more than one, are represented by a single line 52 for ease of illustration.

Figure 5:
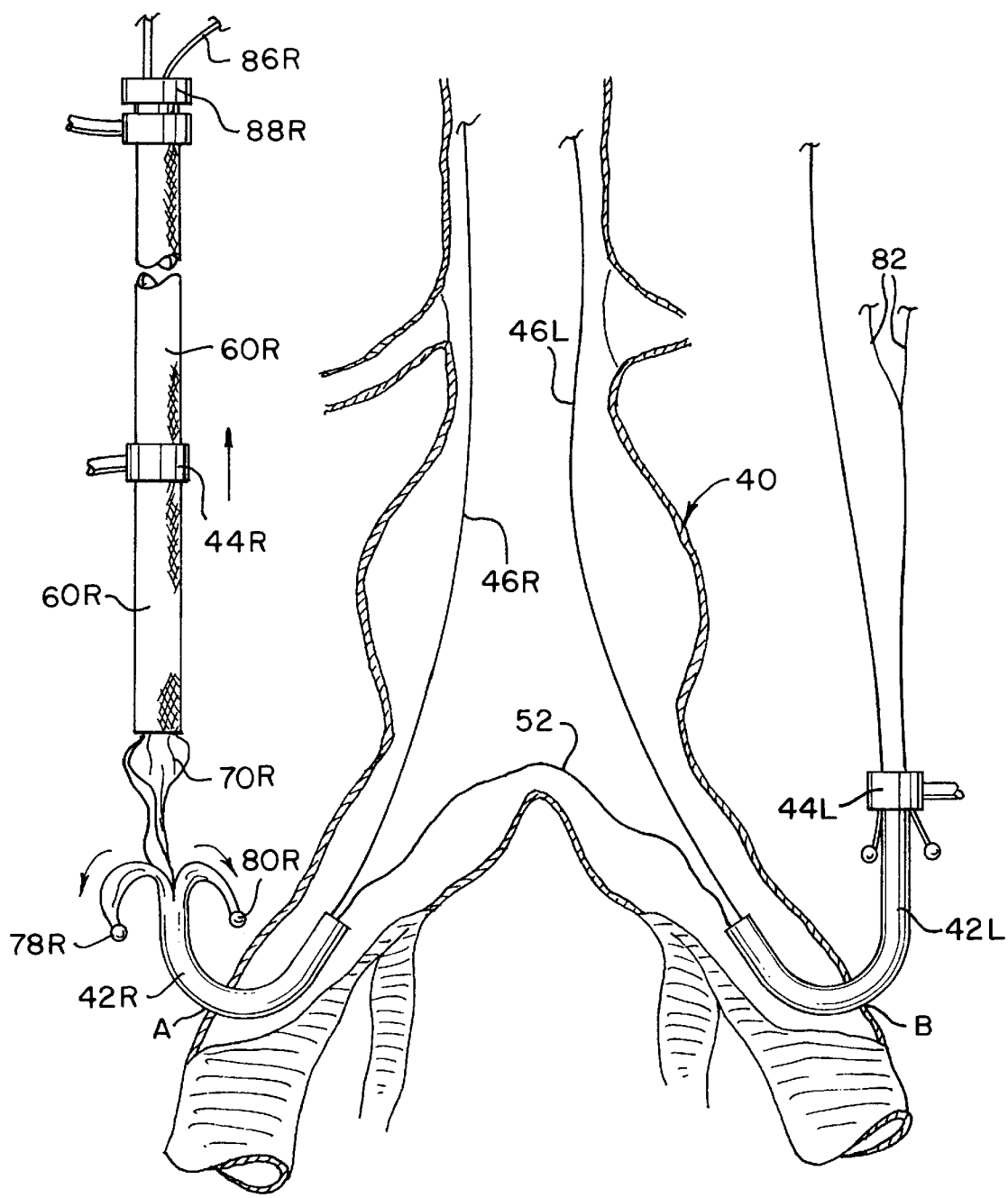
FIG. 5 is the same view as FIG. 3 at a further stage of the method of the present invention wherein a first delivery sheath housing a first graftstent, attached to one end of the anchor line, is being introduced into the patient through the right branch.

In FIG. 5, the valve 44R of the introducer 42R has been positioned over the delivery sheath 60R to permit access to the proximal ends 78, 80 of the introducer 42, such that the introducer 42 can be peeled from the aortic guidewire 46 and anchor lines 52. The proximal ends 78,80 of the introducer 42R have been peeled away while the delivery sheath 60R has been introduced through the femoral cut-down point A. To help minimize back bleeding during the peel-away maneuver, the tip of the lead balloon 70 is made long enough to be inserted into the femoral artery before the introducer sheath 42 is peeled away. Also, the tip of the lead balloon 70 is preferably large enough to occlude the lumen of the peel-away introducer 42. Once the introducer 42 is peeled away, the delivery sheath 60R is advanced through the right femoral artery, the right iliac artery, through the aneurysm and to a point proximate to the renal arteries. The sheath 60 is advanced with fluoroscopic assistance, in a conventional manner. All the while, the lead balloon 70R remains inflated to provide a smooth, atraumatic entry into the patient. Also, any slack in the anchor lines 52 within the patient during advancement of the distal tip of the delivery sheath 60R is taken up by pulling or paid out by pushing the ends 82 of the anchor lines 52 that extend out the left branch so that light tension is maintained on the anchor lines 52. Further, when the aortic stent 64 is made from a nickel-titanium alloy (e.g., nitinol), cold saline or other liquid may be infused through the delivery sheath 60 to maintain the aortic stent 64 below its austenitic transition temperature if processed to exhibit a shape memory change, or to keep it more flexible if processed to be superelastic. Infuseate will escape into the vascular system at the distal end of the sheath 60, for example, through access slot 96 or anchor line port 98 (see FIG. 8), or between the distal end of the delivery sheath 60 and the lead balloon 70.

The graft 66 is attached at its distal end 84 to the aortic stent 64. Preferably, the distal end of the graft 66 is cut on a bias relative to its longitudinal axis, in the manner described in the aforesaid U.S. Pat. No. 5,507,769, such that one margin of the graft extends further along the length of the aortic stent 64 than an opposing margin.

The graft 66 preferably comprises a thin-walled, woven graft of polyester, but may be a conduit made of any one of a variety of artificial materials and even may be autogenous (that is, come from the patient's body). In a preferred embodiment, the polyester graft material is woven to a thickness of approximately 0.1 mm and has a plain weave of 40 Denier yarn, 120 ends/inch, 110 picks/inch. Other materials are contemplated such as expandable polytetrafluoroethelyne (ePTFE). Suitable vascular graft materials that may be used include Model 80S07TW by Impra, of Tempe, Arizona; and Model VT06070L by W. L. Gore, of Flagstaff, Ariz.

Figure 27:
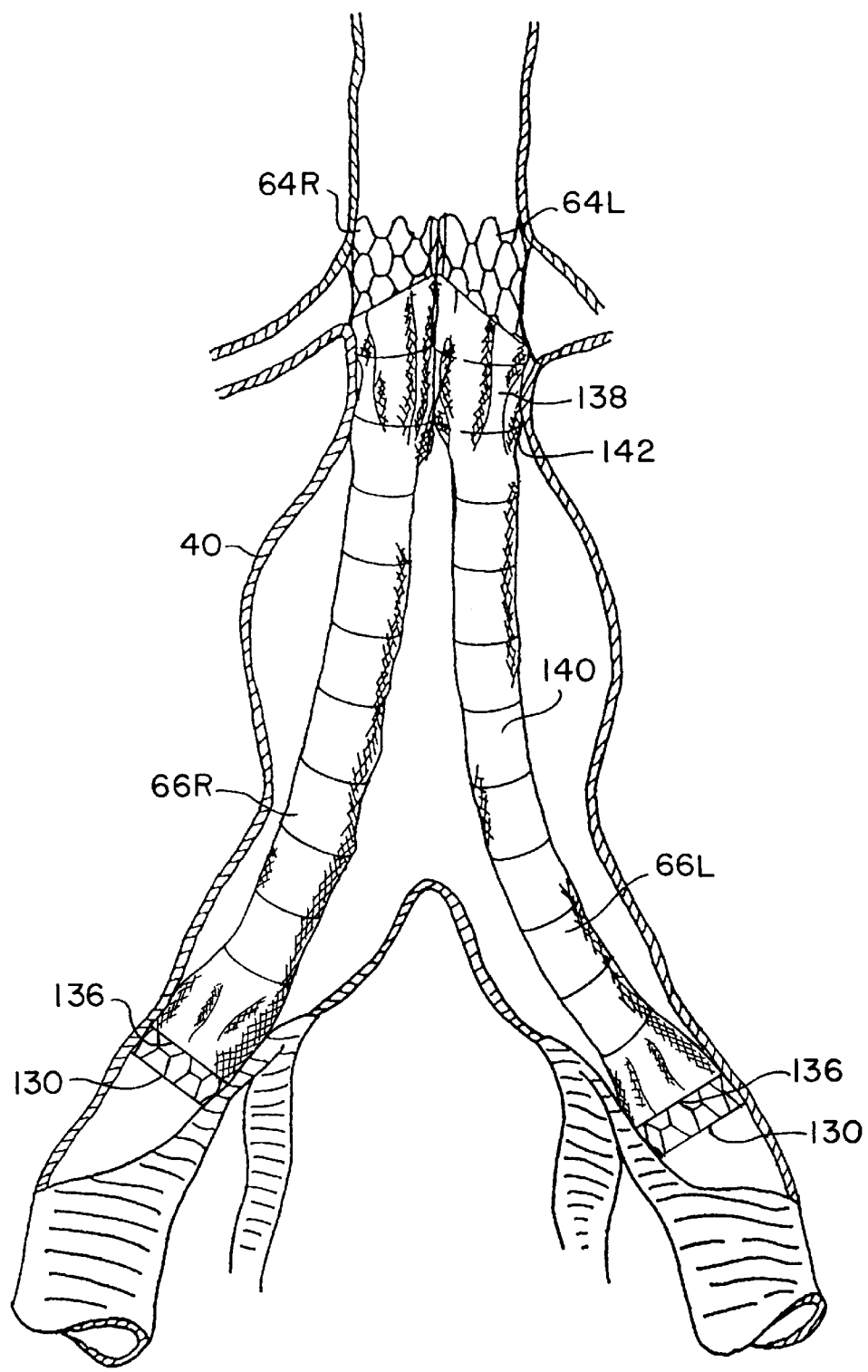
FIG. 27 is the same view as FIG. 26 at a further stage of the method of the present invention wherein each graft has been cut and a caudal stent expanded from within the graft to attach the caudal end of each of the left and right graftstents, and wherein all other devices have been removed from the patient.

The graft 66 comprises several segments of material including a first segment having a diameter suitable for anchoring to healthy tissue in the aorta. Because two grafts will be deployed collaterally within the aorta, neither will have a true circular diameter but rather will form a double-"D" configuration, as shown in FIG. 24. A second segment of the graft has a diameter that is suitable for positioning within the common or external iliac arteries, preferably cephalic of the internal iliac arteries so as not to block blood flow through these arteries. Because the aorta has a nominal diameter that is greater than that of the iliac arteries, the first segment of graft material has a diameter greater than the second segment of graft material. The diameter of the first segment of the graft 138 (that is, at its aortic inlet (see the cephalic end in FIG. 27, for example)), may be "D" shaped and approximately 16 mm×32 mm. When the two "D" shaped graftstents are collaterally deployed, as shown in FIG. 24, they form a circular shape approximately the largest anticipated diameter of the aorta (e.g. approximately 32 mm in diameter). If the aortic diameter is less than 32 mm, any excess graft material is simply left as folds in the wall of the graft 66. Therefore, the graftstent 62 can be sized to fit a range of aortic diameters. Likewise, the second segment 140 of graft 66 may be approximately 12 mm in diameter and may be-inserted into an iliac artery that is smaller than 12 mm in diameter. Under those circumstances, the excess graft material remains folded. Further, an intervening segment 142 of tapering material preferably is provided to smooth the transition between the first and second segments of graft material. he overall length of the first and second graft segments 138, 140, including any transition segment 142, typically is about 30 to 40 cm.

Figure 6:
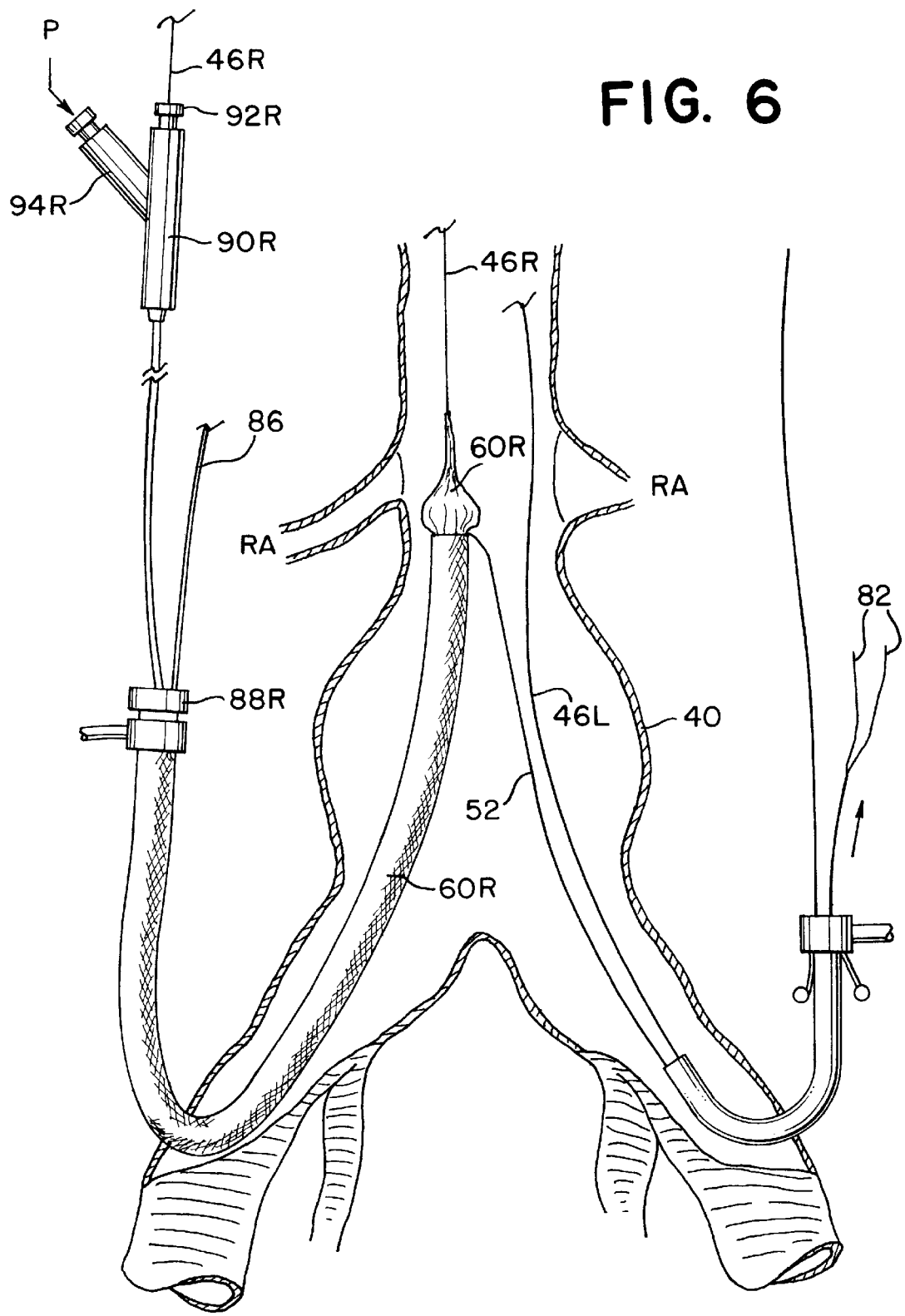
FIG. 6 is the same view as FIG. 5 at a further stage of the method of the present invention wherein the introducer has been removed and the delivery sheath has been advanced to a position proximate the renal arteries.

In addition, the graft 66 includes an elongated line or tab 86 which extends beyond the proximal end 88 of the delivery sheath 60R, as shown in FIGS. 5 and 6, and external to the patient. Once the aortic stents 64 have been expanded, one end of each graftstent 62 is anchored relative to the patient and tension applied external to the patient on the tab 86 positions the caudal end of the grafts 66 relative to the stents 64. Thus, the grafts 66 can be positioned within the patient's anatomy until the desired positioning is achieved. An in situ cutter, described below, can be advanced over the tab 86 to cut the graftstent 62 to size.

In the preferred embodiment, the graft 66 includes circumferential reinforcement hoops (e.g., hoops of nickel-titanium wire) along its length to minimize twisting, collapse and kinking of the graft during delivery, placement, and implantation. Greater than 1 cm spacing does not provide adequate kink resistance especially in view of the tortuosity of the aortoiliac junction; however, a 0.5 cm spacing is believed to be sufficient. A special result is obtained by positioning the hoops approximately every 0.5 cm. Specifically, the graft 66 can fold within the delivery sheath and be readily introduced through the iliac arteries to the aorta, and, upon release of the graftstent 62 from the delivery sheath 60, the graft opens to form a patent lumen without twists or kinks. If the graft is a woven tube, the reinforcing hoops can be incorporated directly in the weave, by periodically replacing the circumferentially oriented yarn (which is on the "shuttle" of the loom) with the nickel-titanium wire. The wire can be woven for a small number of turns, and then ended, resuming the polyester yarn.

FIG. 6 further shows the proximal end of the lead balloon catheter 68 which includes a Y-connector having two inlets: a first inlet 92 which communicates with the lumen 76 for receiving the aortic guidewire 46, and a second inlet 94 which is in communication with an inflation lumen in the lead balloon catheter 68 for delivering a source of pressurized fluid P to the lead balloon 70. The first inlet 92 can also be used for injecting contrast medium into the aorta as an assist in identifying the location of the renal arteries, and, in turn, proper placement of the graftstents 62. Unless the delivery sheath is constructed as a peel-away design, the lead balloon catheter 68 must be approximately two times the length of the graftstents 62 and delivery sheaths 60 so that the delivery sheaths 60 can be withdrawn over the lead balloon catheter. In any event, the lead balloon catheter 68 should have a relatively stiff shaft to hold its position as the delivery sheath is withdrawn and the graftstents 62 are exposed. A suitable material for the shaft of the lead balloon catheter 68 is stainless steel hypodermic tubing, or. braid-reinforced polyimide tubing.

Figure 7:
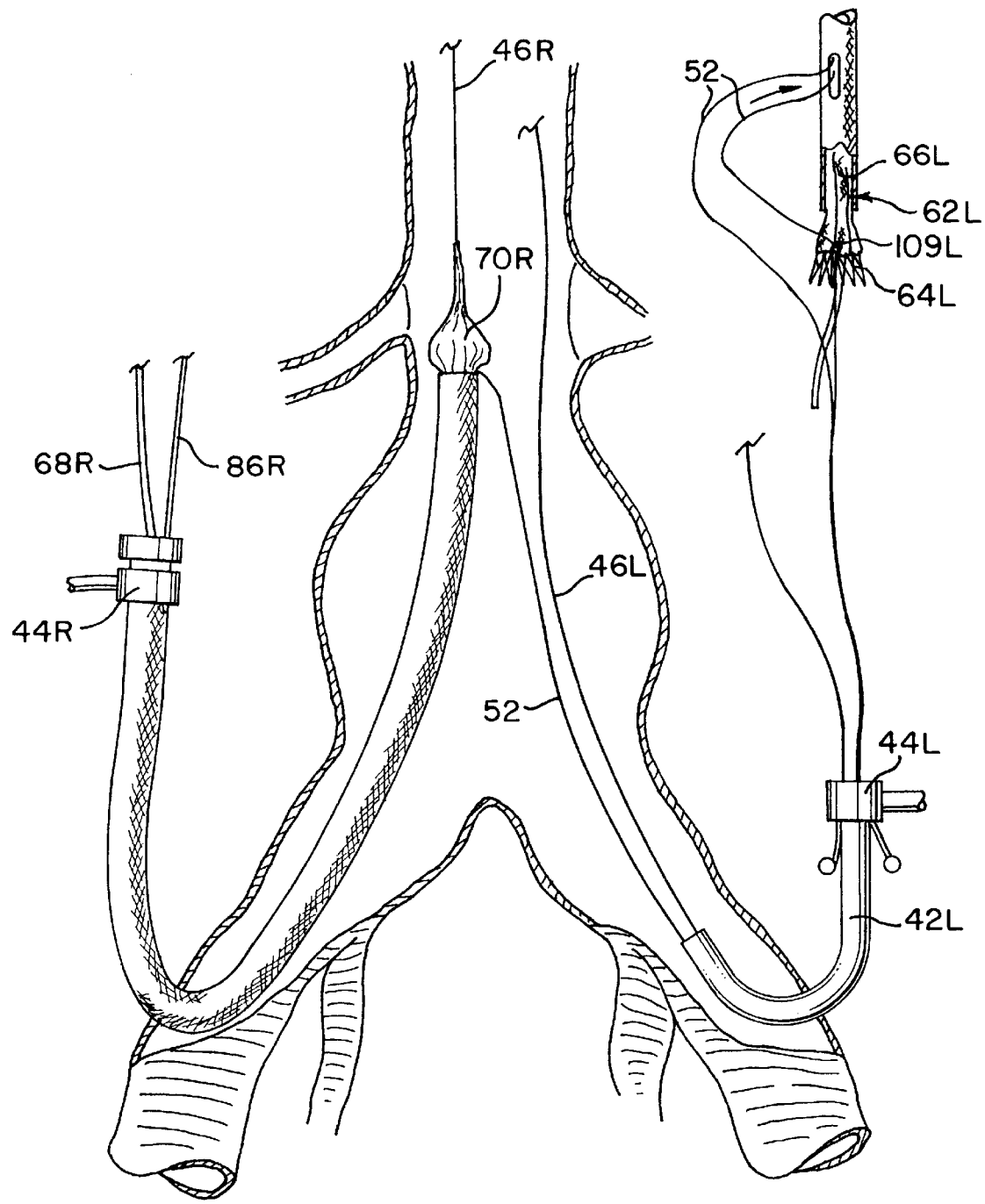
FIG. 7 is the same view as FIG. 6 at a further stage of the method of the present invention wherein the other end of the anchor line is threaded through a second graftstent housed within a second delivery sheath.

In FIG. 7, anchor line ends 82 are threaded through a second graftstent 62L, which comprises an aortic stent 64L and a folded graft 66L, through a preferably radiopaque portion 109 of the graft 66. (Here, the proximal end 90R of the lead balloon catheter 68R is not shown for the sake of simplicity. In addition, the proximal end of the graft 66R is not shown.) The second graftstent 62L is mounted in a delivery sheath 60L for introduction into the patient through the left branch. The graftstent 62L and the delivery sheath 60L are essentially the same as graftstent 62R and delivery sheath 60R, respectively. To facilitate threading of the anchor lines 52, the delivery sheath 60L is retracted to fully expose the anchor site. This is shown in FIG. 7. (FIG. 8 shows the delivery sheath in its fully advanced position, the position for delivery into the patient.)

With further reference to FIG. 8, the delivery sheath 60L is shown having a slot 96 which provides access to the graftstent 62L while containing the graftstent within the delivery sheath 60L. The graftstent 62 is rotationally positioned within the delivery sheath 60 such that the slot 96 is aligned with the straight edge of the aortic stent 64. The anchor line 52 is shown threaded through the graftstent 62L in the vicinity of the slot 96L. If plural anchor lines 52 are provided, then plural slots 96L may also be provided to accommodate and facilitate the threading of additional anchor lines 52 through the graftstent 62L. The delivery sheath 60L further has an anchor line port 98 disposed in the side of the delivery sheath 60L, at a location near the distal end of the delivery sheath 60L. A snare catheter 99 may be disposed within the delivery sheath 60L between the sheath and the folded graft 66L with a snare 101 generally aligned with the anchor line port 98. Once the anchor lines 52 have been threaded through the graftstent 62, and most preferably through the graft 66, the anchor lines are inserted into the snare 101 and withdrawn through the space between the delivery sheath 60L and the folded graft 66 until the ends 82 of the anchor lines extend out the proximal end of the delivery sheath 60L (see FIG. 10).

Figure 9:
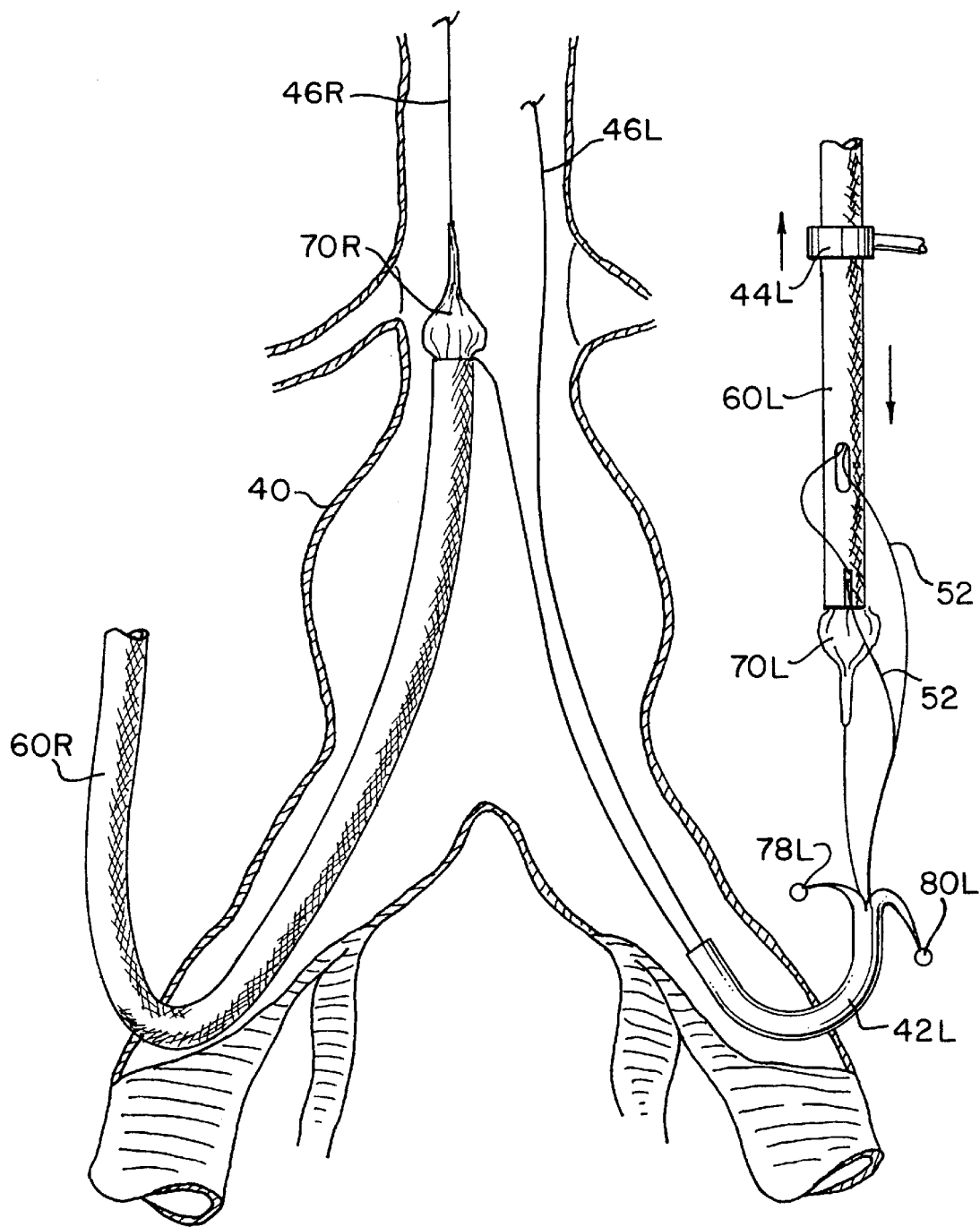
FIG. 9 is the same view as FIG. 7 at a further stage of the method of the present invention wherein the second delivery sheath is being introduced into the patient through the left branch.

With the anchor lines 52 threaded through the delivery sheath 60L, the delivery sheath 60L is ready to be introduced into the patient through the left vascular branch. FIG. 9 illustrates a process similar to that described above with regard to FIG. 5: valve 44 is slid over the delivery sheath 60L and the ends 78L, 80L of the introducer 42L are peeled away while (1) the inflated lead balloon 70L is advanced through the femoral cut-down site, (2) while cool saline solution is infused, (3) and while slack in the anchor lines 52 is taken up.

Figure 10:
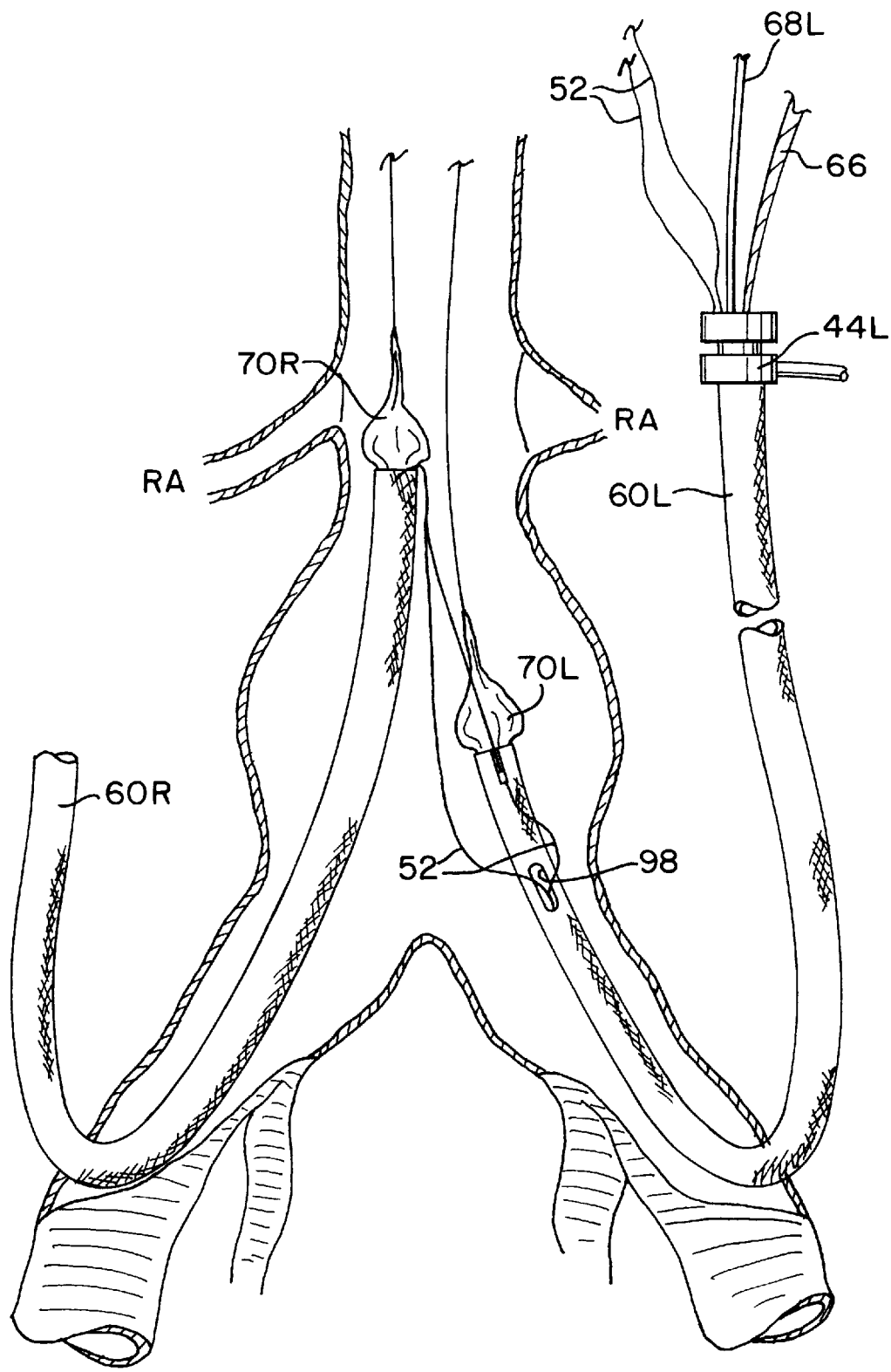
FIG. 10 is the same view as FIG. 9 at a further stage of the method of the present invention wherein the second delivery sheath is being advanced toward the renal arteries.

FIG. 10 shows a further stage of the method after the introducer 42 has been peeled away and the delivery sheath 60L has been advanced through the femoral cut-down site past the iliac arteries and toward the renal arteries RA. While the delivery sheath 60L is advanced into the patient, the anchor lines 52 are held generally taut by taking up the slack as the delivery sheath 60L is advanced. For simplicity, the proximal end of the lead balloon catheter 68L and the graft 66L are not shown.

Figure 11:
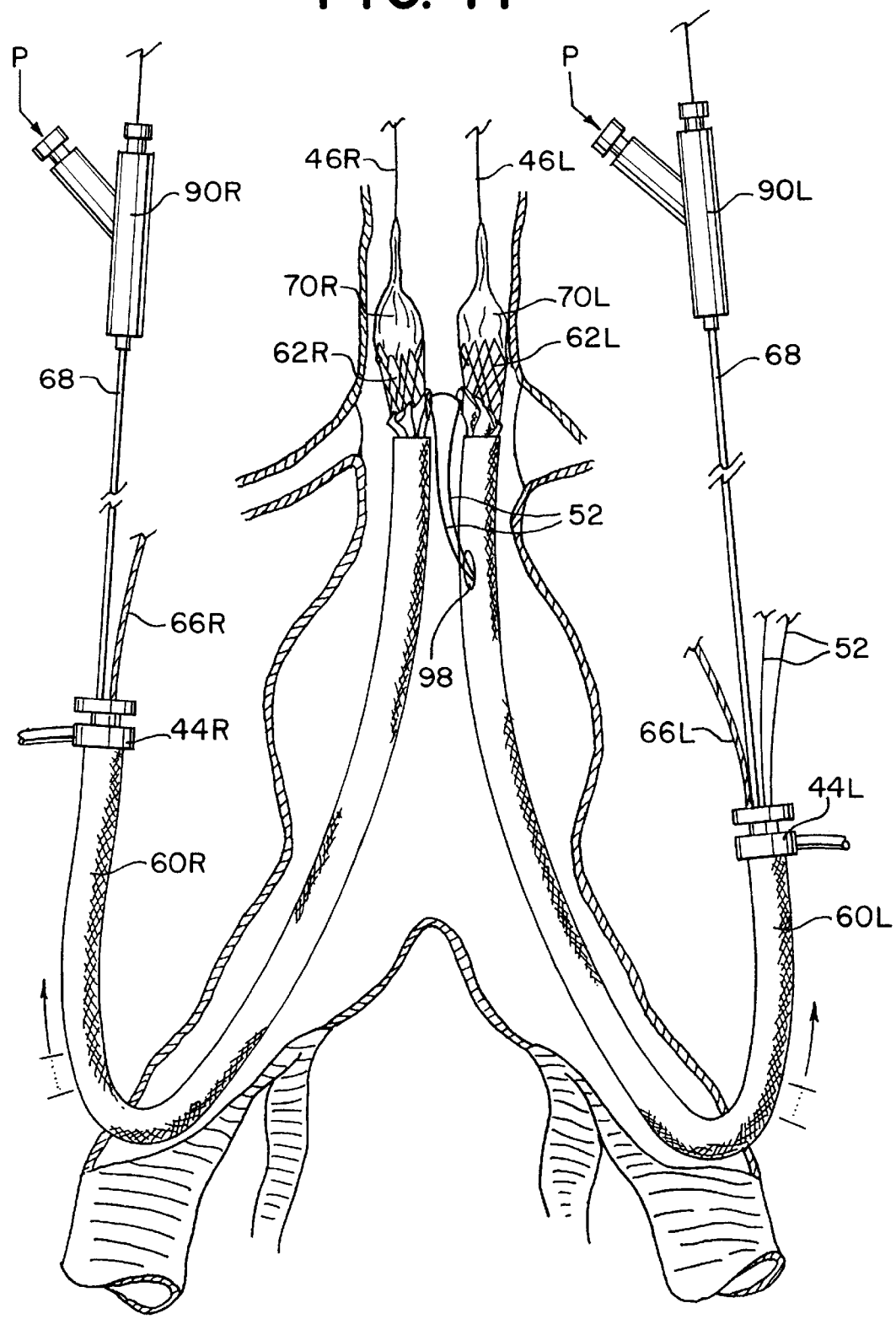
FIG. 11 is the same view as FIG. 10 at a further stage of the method of the present invention wherein the first and second delivery sheaths are both positioned proximate the renal arteries.

In FIG. 11, the delivery sheath 60L has been advanced to a position proximate the renal arteries and alongside the delivery sheath 60R. In addition, the delivery sheaths 60L, 60R have been partially withdrawn while holding the lead balloon catheter 68 in place. By retracting the delivery sheaths 60 relative to the lead balloon catheter 68, the graftstents 62 are partially ejected from the delivery sheath 60 due to the engagement of the ledge 72 of the lead balloon catheter 68 with the proximal edge 74 of the aortic stent 64. As a result, the anchor line attachment point 106 (and any additional anchor line attachment points) are exposed to facilitate alignment and anchoring the left and right graftstents 62 together, as discussed next. Preferably, the attachment point 106 and any additional attachment points are located on the graft 66 along with a radiopaque marker 107 made of a radiopaque material (see FIG. 14).

Figure 12:
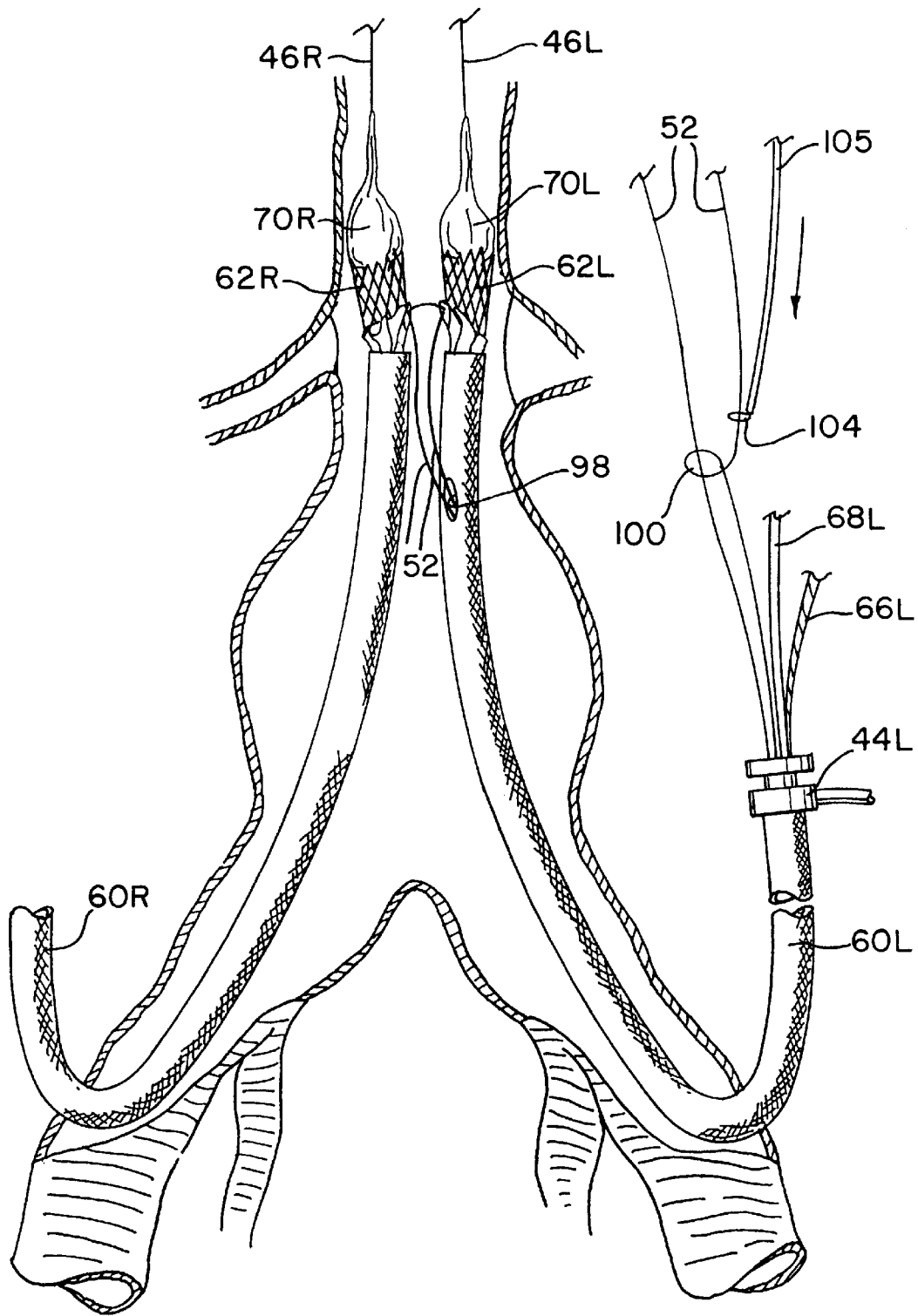
FIG. 12 is the same view as FIG. 11 at a further stage of the method of the present invention wherein the knot is being advanced over the anchor line as one approach to securing the first and second graftstents together in accordance with an aspect of the invention.

In FIG. 12, a slidable knot 100 has been formed in one of the anchor lines 52 about another anchor line 52. A pusher 102 having a wire tracking element 104 at the distal end of a rigid, elongated rod 105 (which may be about 50 cm or longer in length) is positioned over the proximal ends 82 of one of the anchor lines 52 and used to push the slidable knot 100 distally into the proximal end of the delivery sheath 60L and out through the anchor line port 98 until the slidable knot 100 engages the first graftstent 60R.

Figure 13:
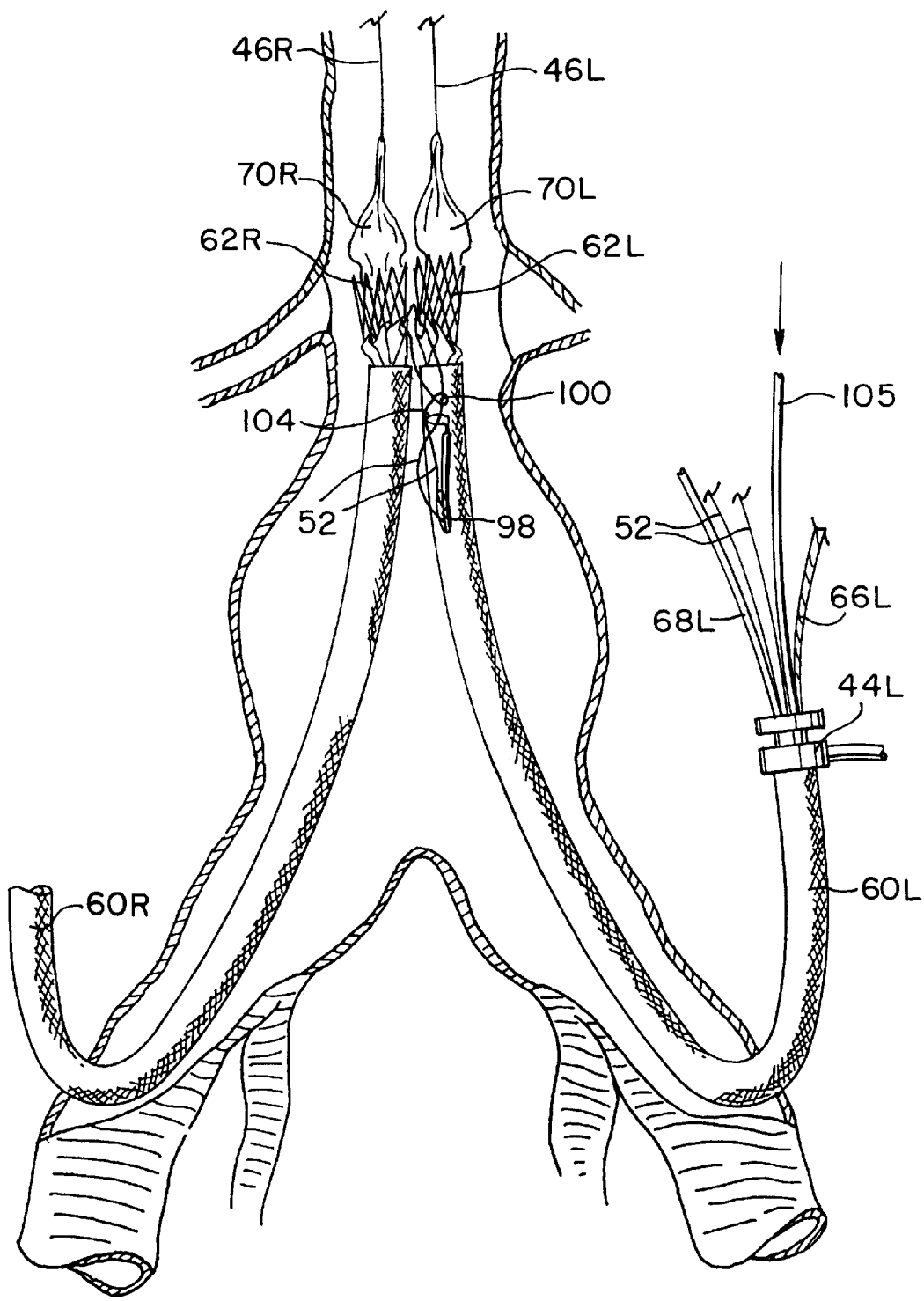
FIG. 13 is the same view as FIG. 12 at a further stage of the method of the present invention wherein the knot has been advanced through the left delivery sheath to a position proximate the first and second graftstents.

In FIG. 13, the wire tracking element 104 emerges from the anchor line port 98 and the slidable knot 100 is now in the vicinity of the distal end of the delivery sheath 60L. The detailed view of FIG. 14 shows the wire tracking element 104 advancing along one of the anchor lines 52 to push the slidable knot 100 toward a secured knot point 106 on the graft 66R of the first graftstent 62R. As the pusher 102 is advanced, the left and right graftstents 62R, 62L come together and the length L of anchor line 52 extending between the two graftstents 62L, 62R reduces. In this manner, the knot is secured between the two graftstents 62 at a position just below the inlets 105 (see FIG. 23) of the aortic stents 64. The knot does not reside within either blood flow lumen of the graftstents 62. In addition, as the length L between the left and right graftstents 62 decreases, the straight edge of each aortic stent 64 rotates to face one another because the anchor point 106 is drawn close to the threaded coupling in the slot 96.

Figure 15:
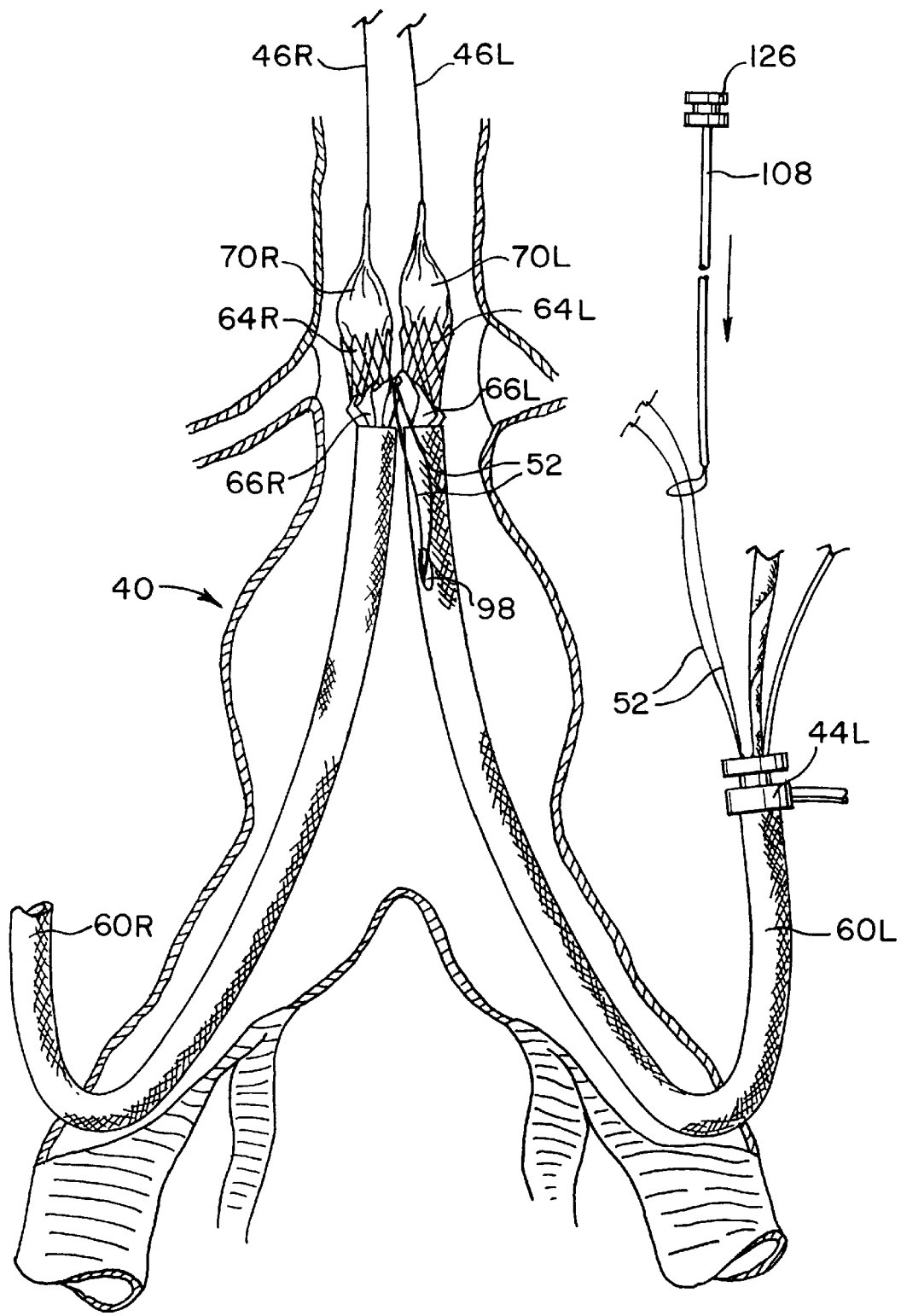
FIG. 15 is the same view as FIG. 14 at a further stage of the method of the present invention wherein the knot has been fully advanced so as to draw the first and second graftstents together, and wherein a cutting device is being advanced over the anchor lines.

In FIG. 15, the slidable knot 100 has been fully advanced along the anchor guidewire 52 such that the length L has been reduced to zero whereby the left and right graftstents 62L, 62R have been fully drawn together, and the knot ties the graftstents 62 together. To further secure the graftstents 62 together, additional knots can be tied and advanced in a similar manner. At this stage, a cutting device 108 can be introduced over the ends 82 of the anchor lines 52 for cutting away the excess: length of anchor lines 52 extending from the knot thus formed (see FIGS. 19–21).

Figure 16:
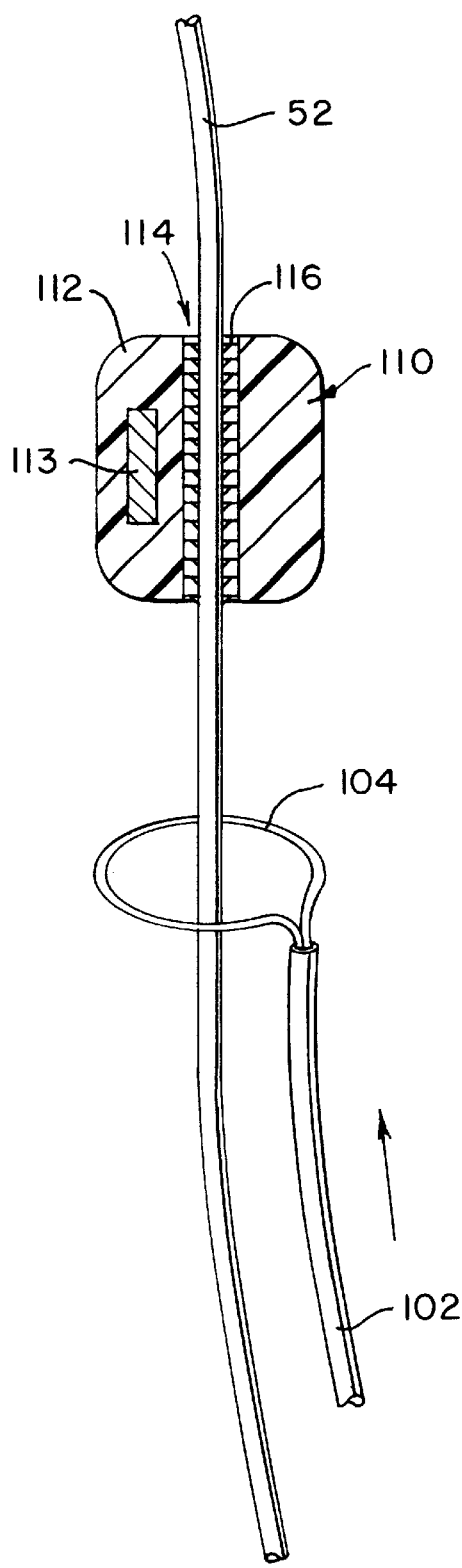
FIG. 16 is a detail view of a anchor bead according to another aspect of the present invention which can be advanced along the anchor lines using the pusher instead of or in addition to one or more knots.

FIG. 16 is a detailed view of a slide or anchor bead 110 according to another aspect of the present invention which can be advanced over the anchor line 52 using the pusher 102 in lieu of, or in addition to, the slidable knot 100. The anchor bead 110 is constructed to slide along the anchor line 52 in one direction only so that it can be advanced relative to the anchor line 52 toward, for example, the anchor line's attachment point 106 on the graft 66R.

The anchor bead 110 comprises a body 112 having an axially directed aperture 114 extending from one end to another. Preferably, the anchor bead 110 is made from a biocompatible material such as polypropylene or polyethylene. The long-term stability of the material chosen for the body 112 of the anchor bead 110 is not critical to the inventive method. Rather, the anchor bead and anchor sites are used merely to facilitate the initial placement of the graftstent. Over time, the arterial wall will heal through the wall of the stent and provide a secure anchor.

Figure 16A:
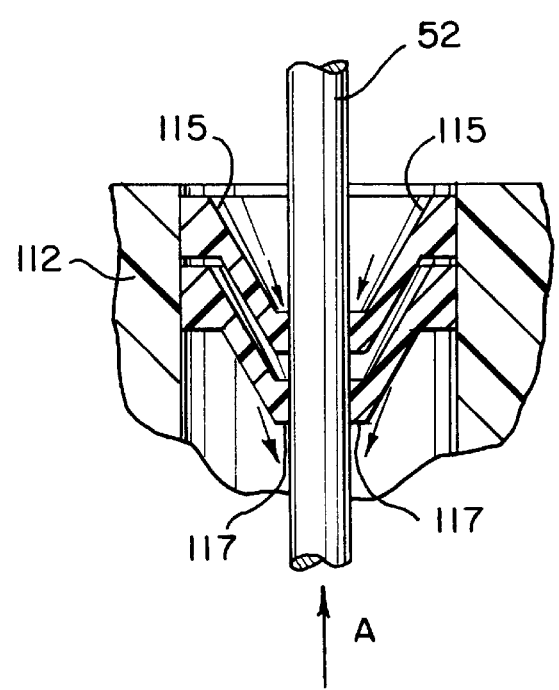
FIG. 16a is a detail view, in cross section, showing the arrangement of the seals of the anchor bead relative to the anchor wire.

A plurality of elastic seals 116 line the aperture 114. The seals 116 have an opening oriented in same axial direction as the aperture in the body 112 which is sized to receive an anchor line 52. The seals 116 are preferably formed of a resilient and elastic material such as silicone rubber or polyurethane. The seals 116 are arranged to permit movement of the body 112 relative to the anchor line 52 in a first axial direction and to restrict relative movement of the body 112 relative to the anchor line 52 in a second axial direction, opposite the first axial direction. Preferably, the seals 116 have an axially-asymmetric shape, for example, the shape of a funnel, as can be seen in FIG. 16a. The funnel shape, for example, allows the anchor line 52 to be readily funnelled through the aperture 114 of the anchor bead 110, that is, to move through the major (wide) orifice 115 toward the minor (narrow) orifice 117. However, movement of the anchor line 52 in the opposite direction causes the seals 116 to flex and the side walls 117 of the minor orifice to bind against the anchor line 52 (see detail of FIG. 16a and arrows). The binding action of the seals 116 restricts motion of the anchor wire 52 in the direction of arrow A (FIG. 16a), and prevents the anchor bead 110 from retracting from the position to which it has been advanced.

Preferably, the anchor bead 110 includes a radiopaque element or material 113 included in the body 112. For example, barium sulfate can be incorporated into the polymer of the body 112, or a platinum, tungsten or other radiopaque element 113 may be housed within the body 112 (as shown in FIG. 16) or on its circumference. Certain advantages result by associating a radiopaque element 113 with the anchor bead 110. Of particular importance with regard to the present invention is that it enables the operator to visualize on a fluoroscope whether the left and right graftstents 62 have been completely sinched together, especially when the attachment points 106, 109, 111, 118, and 120 (see FIGS. 14 and 18) also include a radiopaque marker because the markers of the left and right graftstents 62L and 62R and the marker 113 of the friction bead 110 all come together as the friction bead 110 is advanced so as to sinch the graftstents 62 together; In addition, the operator can monitor the progress of the anchor bead through the vasculature and determine the source of any impediments that might be encountered (for example, plaque). Also, in the event that one of the anchor lines 52 breaks, the radiopacity of the bead 110 enables the bead 110 to be located within the body passageway for subsequent removal.

In operation, the anchor bead 110 is threaded onto the proximal end 82 of the anchor line 52 and advanced therealong using the pusher 102 through the delivery sheath 60L and out through the anchor port 98 until it contacts the anchor line attachment point 106 on the first graftstent 66R.

Figure 17:
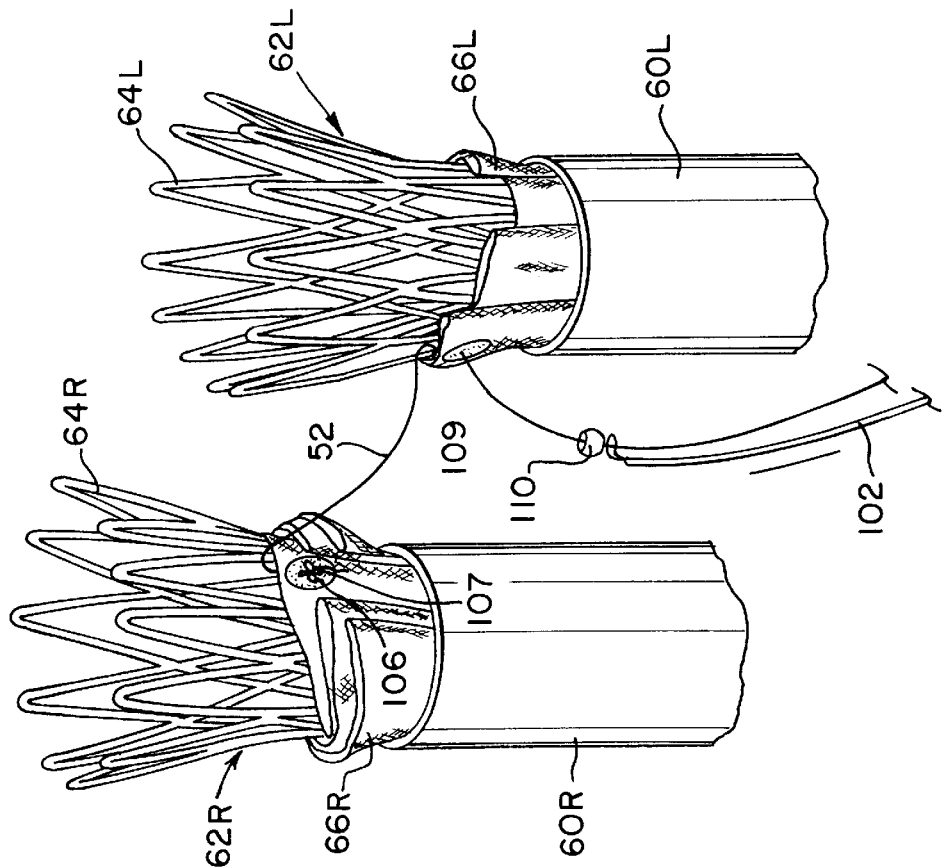
FIG. 17 is a similar view to that of FIG. 14 wherein the anchor bead is being advanced over the anchor line as another approach to securing the first and second graftstents together.

The detail of FIG. 17 generally shows this procedure for the case where a single anchor line 52 is used. It is worth noting that only one anchor line 52 is required for an anchor bead 110 to be advanced toward a single anchor line attachment point as compared to advancing the slidable knot 100 which requires two anchor lines for a single anchor line attachment point. This makes use of the anchor bead 110 comparatively simpler, as there are fewer lines that may potentially twist and increase the difficulty in locating the knot at the anchor line attachment point. A direct advantage of this approach is that multiple anchor points can be used with half as many anchor lines 52. Another advantage of the anchor bead 110 approach is that only one advancement step is necessary, as compared to multiple advancements of slidable knots 100 to suture the left and right grafts 66R, 66L together.

FIG. 18 is a similar view to that of FIG. 17 except that it shows three anchor line attachment points instead of just one anchor line attachment point 106. The additional sites 118, 120, are preferably located at the upper and lower margins of the D-shaped aortic stent 64.

Figure 19:
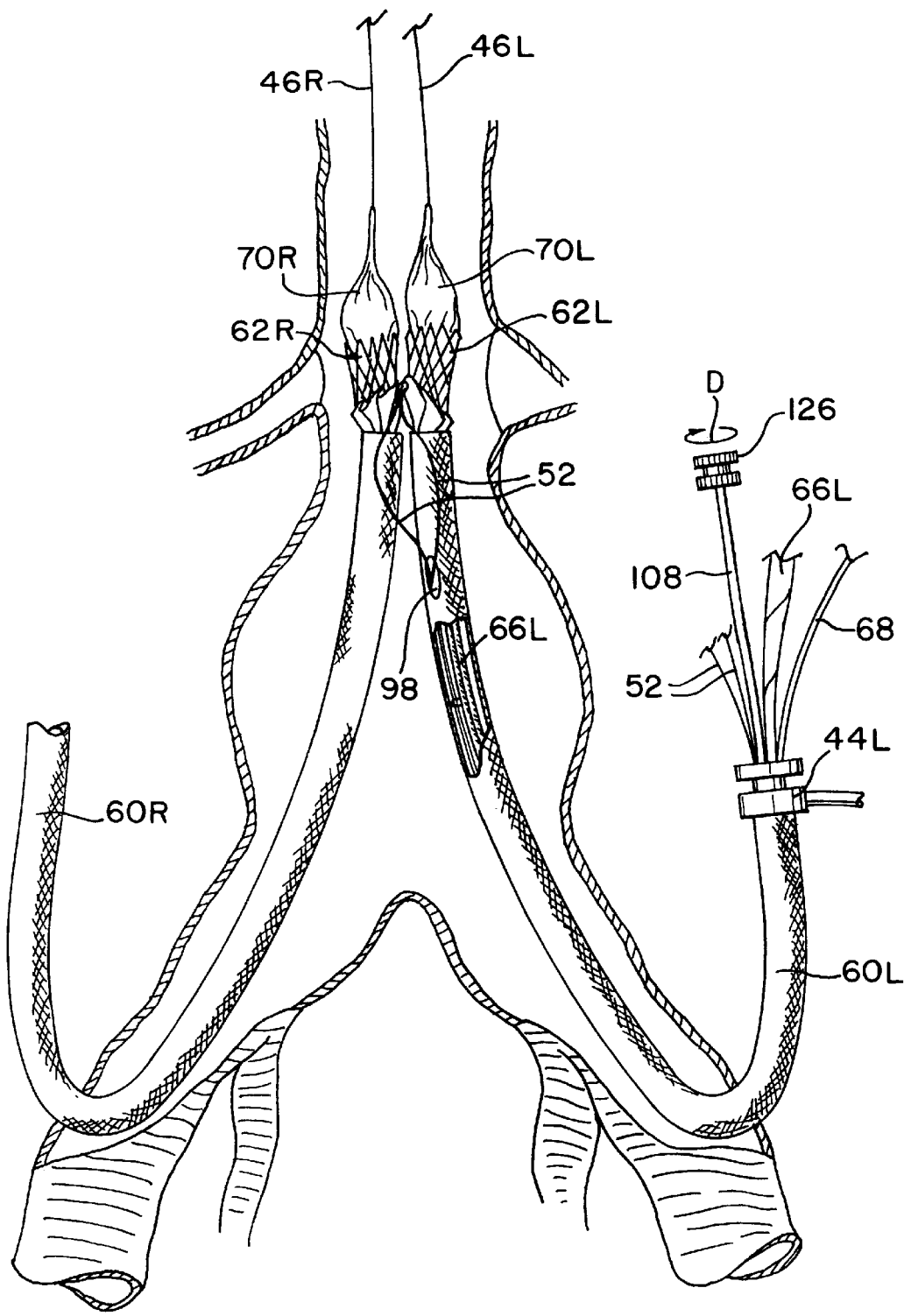
FIG. 19 is the same view as FIG. 15 at a further stage of the method of the present invention wherein the cutting device has been advanced over the anchor lines toward the renal arteries.
Figure 21:
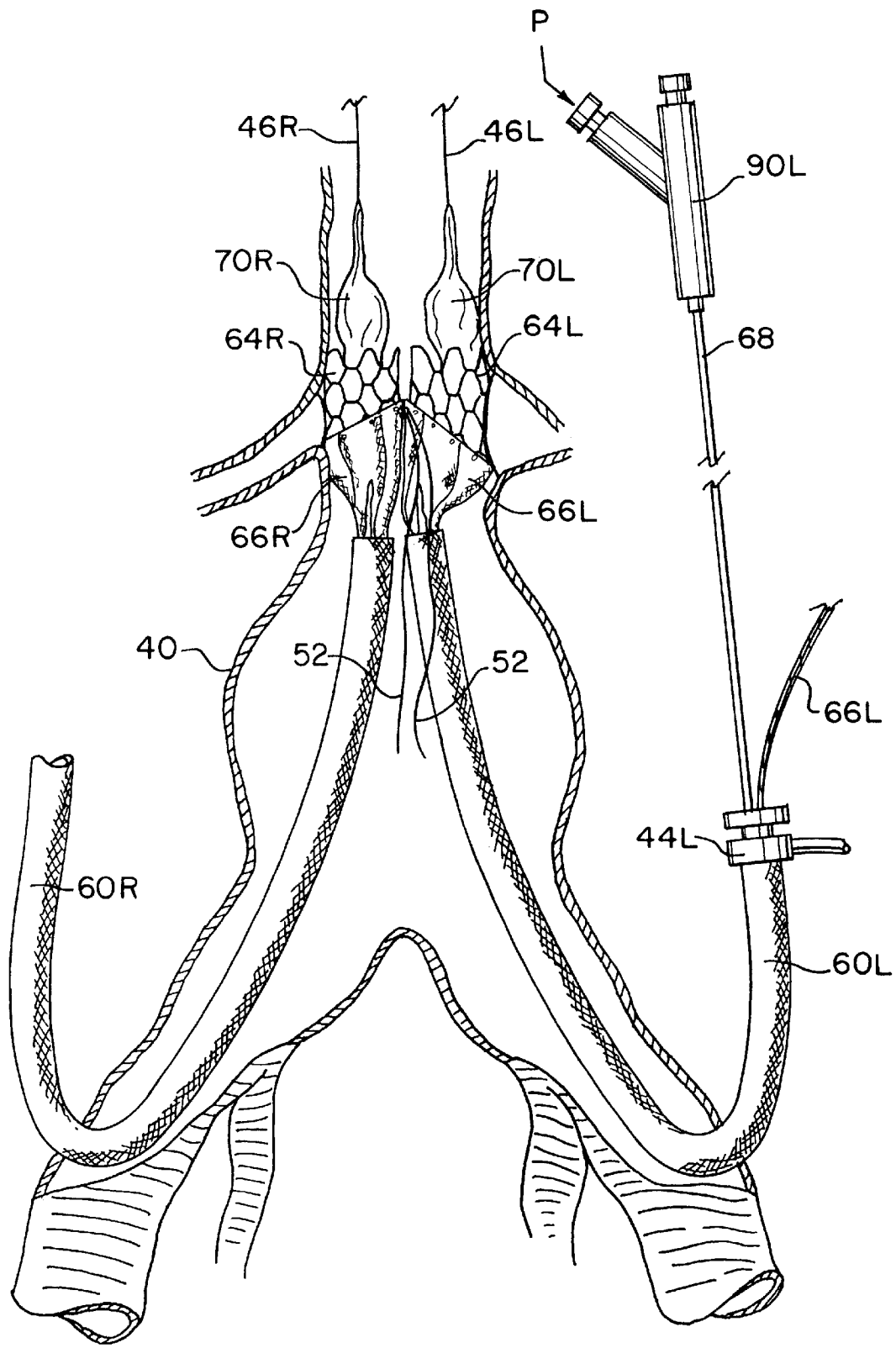
FIG. 21 is the same view as FIG. 19 at a further stage of the method of the present invention wherein the anchor lines have been cut and the cephalic stents have been caused to expand by partially retracting the delivery sheaths relative to the graftstents.

FIGS. 19 and 20 illustrate the cutter 108 having been advanced between the delivery sheath 60L and the folded graft 66L. The cutter 108 has a sharpened element at the distal end thereof. Once the cutter 108 has been advanced to a desired position along the anchor lines 52, the anchor lines 52 are drawn into the distal end 122 of the cutter 108 by the snare 124. As the cutting wires are drawn into the distal end 122 of the cutter 108, the anchor lines are cut. FIG. 21 illustrates the anchor lines 52 after being cut and after the cutter 108 has been withdrawn from the patient. The snare 124 is withdrawn into the distal end 122 of the cutter 108 by, for example, actuating a rotatable member at a proximal end 126 of the cutter 108, as by rotating the rotatable member in the direction of arrow D, as shown in FIG. 19. Numerous examples of cutting devices are described in co-pending U.S. patent application Ser. No. 08/783,174, filed Jan. 14, 1997.

In FIG. 21, the first and second delivery sheaths 60L, 60R have been withdrawn while holding the lead balloon catheter 68L, 68R (and ledge 72) in position so as to cause the aortic stents 64L, 64R to expand. Preferably, the delivery sheaths 60L, 60R are withdrawn simultaneously, but they may also be withdrawn sequentially. The delivery sheaths 60 preferably have visible markings along their respective proximal ends so that the physician can gauge how far the sheaths have been retracted. Preferably, the aortic stents 64 are made of nickel-titanium alloy and have a generally D-shaped configuration in cross-section when expanded such that the curved edge contacts healthy tissue (proximate the renal arteries in the Figures) and the comparatively straight edge of stent 48R contacts the straight edge of the collateral stent 64 at the location of the anchor line attachment points 106 (and perhaps points 118 and 120, etc.) (see FIG. 24). The aortic stents 64 are preferably about 5 cm long. A suitable alloy is one comprising 55.8% nickel (by weight) and the balance titanium. This alloy exhibits "shape memory" properties. A parent shape of an expanded D-shape can be imparted to the stent 64 by annealing the stent 64 on a D-shaped mandrel. The initial diameter stent can be formed by utilizing a small diameter ni-ti tubing (e.g., 3 mm tube having a wall thickness of 0.015 inches), and forming longitudinal slots in the wall using a laser. The slotted walls deform upon expansion, as is known in the art. A cooling solution may be infused through the sheaths 60 to retard expansion of the stents 64 until a desired moment. The individual "D" shaped stents may also be attached to one another and the body vessel by barbs which remain within the surface of the stent when the stent is in its unexpanded condition, but which extend from the surface of the stent when the stent is expanded. A suitable stent of this variety is described in Marin et al. U.S. Pat. No. 5,397,355 for INTRALUMINAL STENT, which issued on Mar. 14, 1995 al., the entirety of which is incorporated herein by reference as if set forth herein. Of course, the "D" stent need not have a straight edge. Other configurations for the straight edge would provide a significant surface for frictional engagement with the adjacent (collateral) expanded stent, for example, sinusoidal, triangular, trapezoidal abutting edges. Of course, if the aortic stents are of the balloon expandable type, they would be mounted on a suitably sized and shaped balloon (e.g., a 16×32 mm balloon).

Preferably, aortic stents 64 include a radiopaque marker such as a wire or other geometric shape made of, for example, platinum or tungsten and located on a curved edge thereof and even more preferably at the mid portion of the curved region and at the cephalic end of the graft 66. The radiopaque markers are fluoroscopically viewable so that the markers on adjacent stents 64 can be oriented to be separated from one another within the aorta at a maximum distance, at which orientation the stents 64 are aligned so that the straight edge of one stent 64 will contact the straight edge of the other stent 64 when expanded. In addition, the location of the markers relative to an internal body passageway (for example, the renal arteries) can be discerned by injecting contrast medium into the passageway which assists in locating the stents 64 within the patient so as to not inadvertently block a side passageway. Instead of providing markers on the stents 64, which is the presently preferred mode of operation, markers can be provided on the grafts 66 or the tools used to introduce the graftstents 62 (for example, the lead balloon catheter 68 or the delivery sheaths 60).

The grafts 66 may also include radiopaque markers so that the operator can discern whether the graft has been deployed free of kinks or twists. As noted above, the resiliently deformable hoops assist in avoiding kinks and twists in the graft.

Figure 24A:
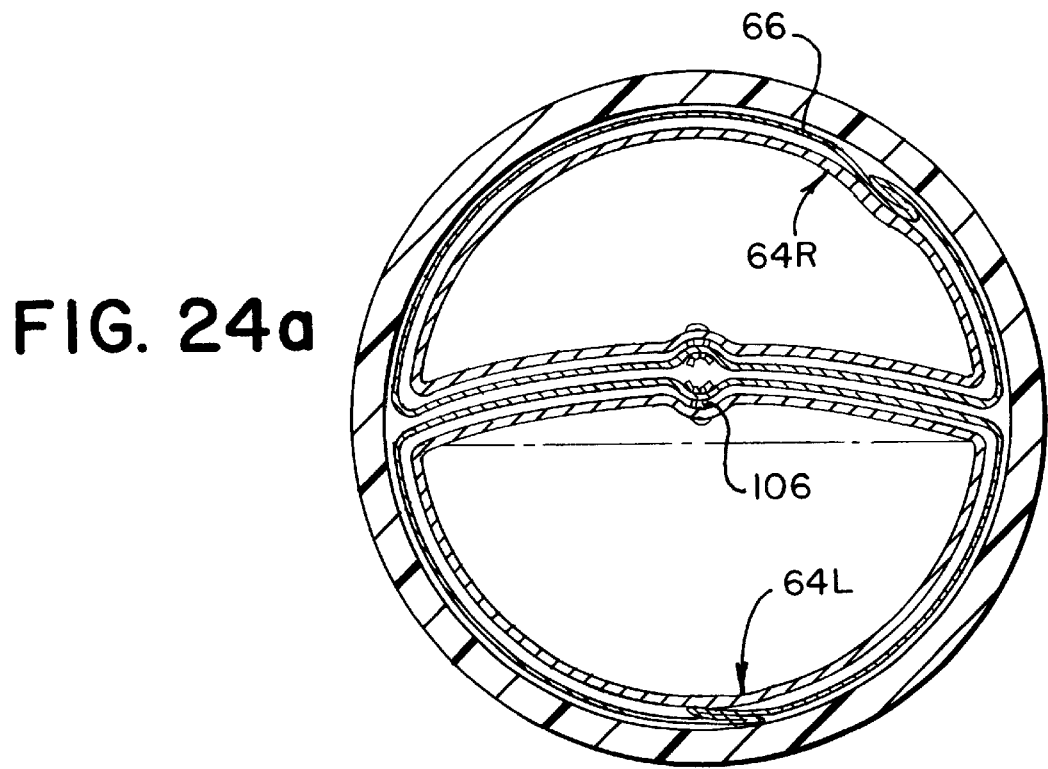
FIG. 24a is also a cross-sectional view taken along lines 24—24 of FIG. 23, and further illustrates a preferred bowing of one margin of the stents.

Over time, the aorta applies forces to the D-shaped aortic stents 64 which tend to cause the straight margin of the aortic stents 64 to bow or buckle to form a curved union between the adjacent stents 64. If the aortic stents 64 have parent shapes that are perfectly straight along their straight margin, the bowing or buckling might result in a gap between the aortic stents 64, particularly if the bowing or buckling of the adjacent stents is not complementary. However, plural anchoring sites 106, 118, 120 reduces buckling and bowing by better sinching together the adjacent stents 64. Alternatively or in addition, a pre-fabricated or preset bow is provided in the straight side of the D-shaped stents. For example, a nickel-titanium alloy stent can have its parent shape formed with a preset bow, as shown in FIG. 24a. The preset bow takes on a common direction and shape in both stents to foster meshing therebetween and greatly reduce the chance for gaps to exist between the adjacent aortic stents 64. As seen in FIG. 24a, stent 64L has a convex bow and stent 64R has a concave bow such that the stents 64R and 64L substantially mate along their common margin.

Figure 22:
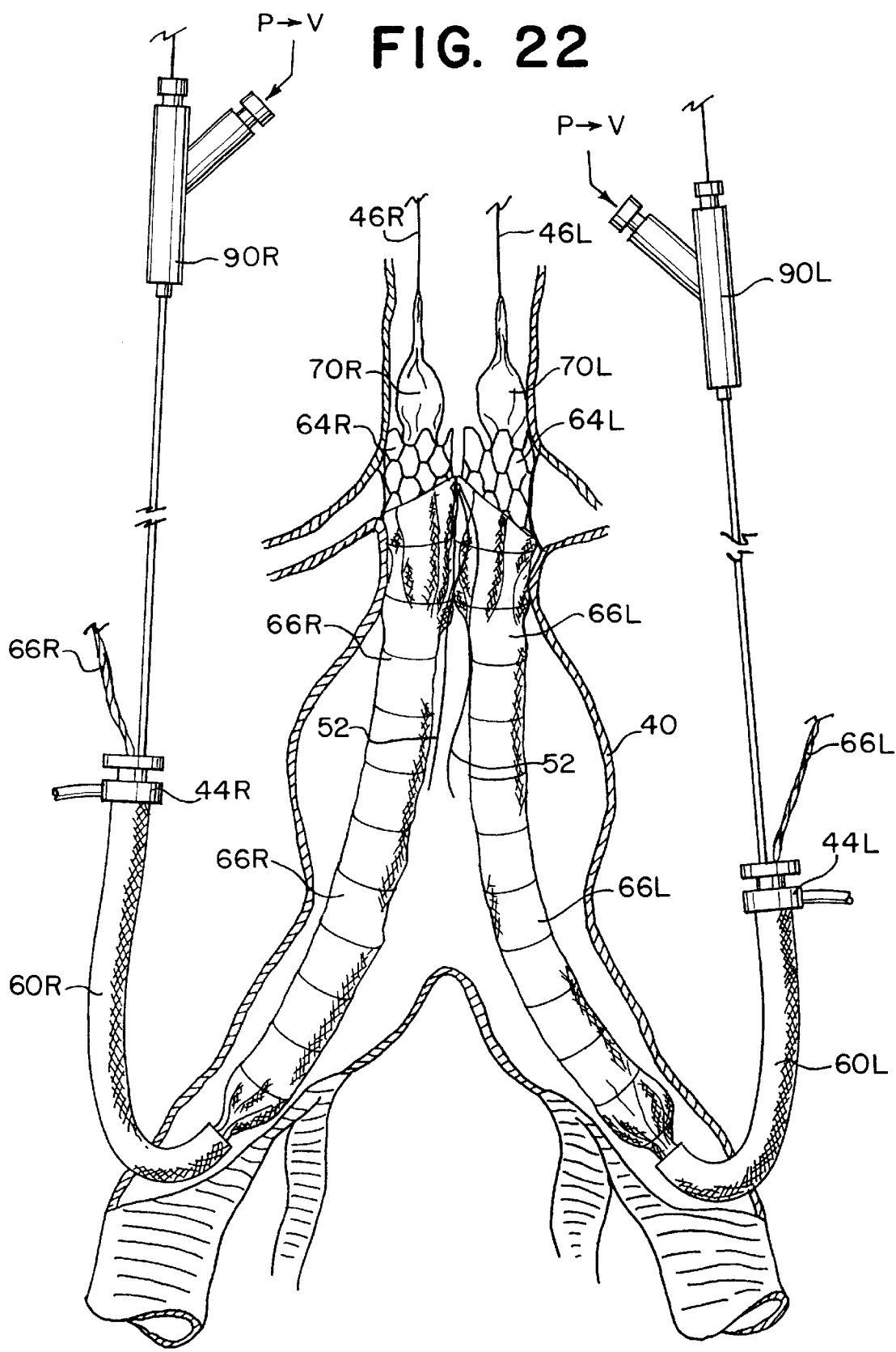
FIG. 22 is the same view as FIG. 21 at a further stage of the method of the present invention wherein the. delivery sheaths have been retracted so as to extend only partially into the femoral arteries and thereby permit the grafts to unfold.
Figure 23:
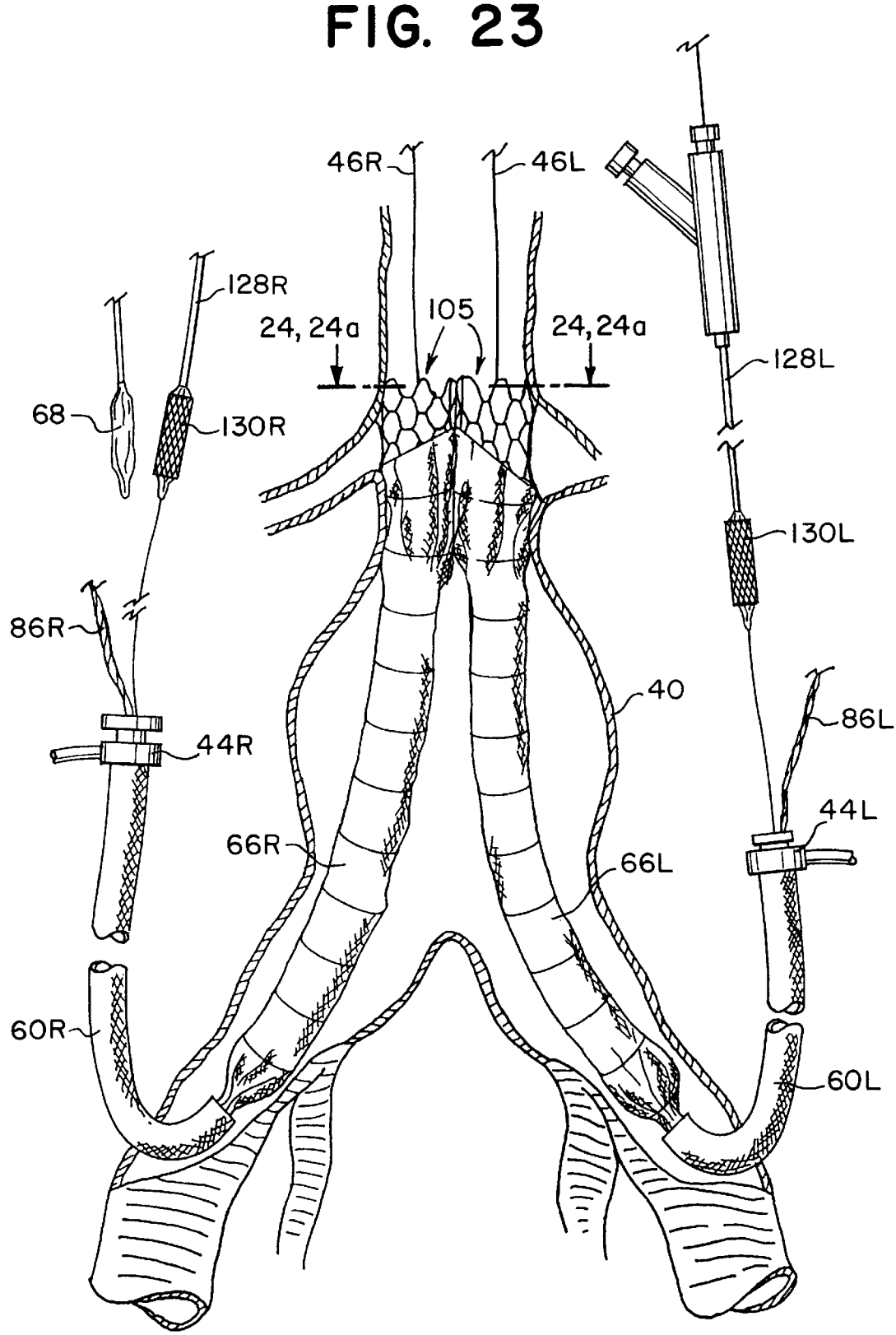
FIG. 23 is the same view as FIG. 22 at a further stage of the method of the present invention wherein lead balloon catheters, previously housed within the delivery sheaths, have been withdrawn from the patient and wherein a stent delivery catheter is being introduced over the aortic guidewires of each of the right and left vascular branches.

In FIG. 22, the delivery sheath 60L, 60R have been withdrawn so that only their distal end remains within the femoral arteries, again as determined with the help of visible markers on the delivery sheaths 60. As a result, the grafts 66 expand within each of the left and right branches. At this stage of the procedure, the lead balloons 70 can be deflated and withdrawn from the graft stents 62, as shown in FIG. 23.

FIG. 22 shows the aortic stents 64 projecting cephalically of the grafts 66. The grafts 66 are also shown with a bias cut, the most cephalic portion of the bias cut being alongside the straight edge of the D-shaped stent 64. FIG. 22 also shows the aortic stents 64 placed across the ostium of the renal arteries. This placement facilitates better anchoring of the graftstents 62 to the aorta by providing more stent surface to engage the aorta.

Providing the graft 66 with a bias cut minimizes the "alloy-to-alloy" contact between the straight edges of the stents 64, while still allowing the renal arteries to be perfused through the stents 64. Full alloy-to-alloy contact is prevented when the bias cut extends to the cephalic straight edge of the stent 64, with the graft 66 disposed between the stents.

However, in some instances, coverage of the renal arteries with stents 64 may not be desirable in which case the stents 64 would project cephalically only a small amount, if at all, and the grafts 66 may have little to no bias cut.

Various combinations of bias cut angle and amount of cephalic projection of stents are contemplated. The amount of cephalic projection also influences the length of the slots 96, as shown in FIG. 8.

FIG. 23 shows the cephalic ends of the graft stents 62 deployed within the patient. The cross-section of FIG. 24 illustrates the cross-section of the aorta with the right and left stents 64 attached at one anchor line attachment point 106 and the grafts 66 of each graft stent 62.

In FIG. 23, stent delivery catheters 128 having a stent 130 at their distal end are respectively loaded onto the aortic guidewires 46. FIG. 23 also illustrates the lead balloon catheters as having been withdrawn from the delivery sheaths 60. The stent delivery catheters 128 are advanced over the aortic guidewires 46 and through the delivery sheaths 60 to a position within the grafts 66 that is generally within the femoral arteries, as shown in FIG. 25. A graft cutting device 132 having a cutting element 134 at its distal end is advanced over the stent delivery catheter 128 and around the caudal end 86 of graft 66 and advanced through the delivery sheath to a position within the femoral artery. A suitable cutting device and procedural steps are described in Marin et al. U.S. application Ser. No. 08/783,174 for METHOD FOR FORMING CUSTOM LENGTH ENDOLUMINAL GRAFT, filed Jan. 14, 1997, the entirety of which is hereby incorporated by reference as if set forth herein. Preferably, the cutting device 132 has a 2 French diameter and includes a lumen through which a contrast solution can be introduced so that the position of the cutting element 134 can be precisely determined by visualization using an arteriogram.

Figure 26:
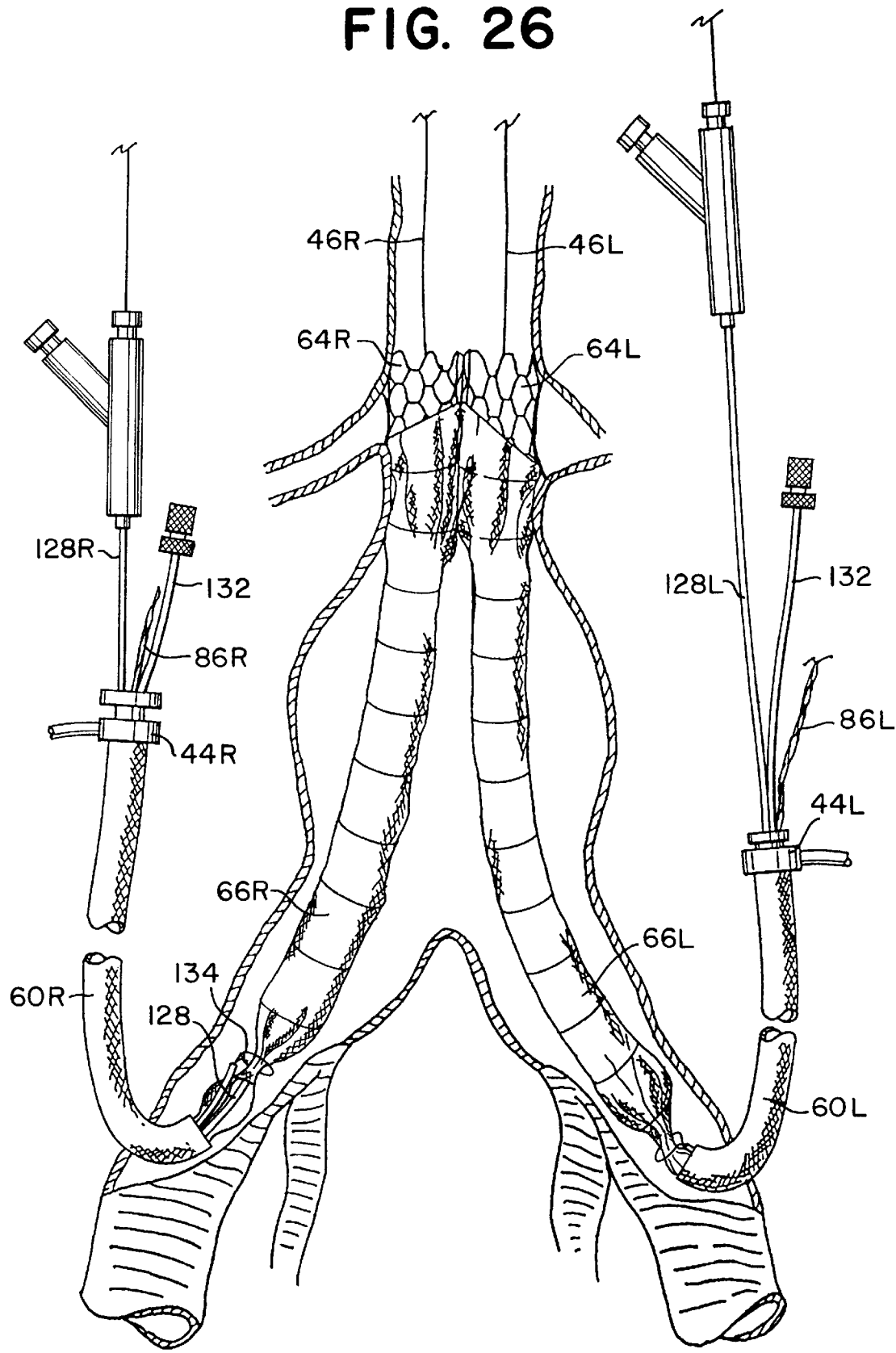
FIG. 26 is the same view as FIG. 25 at a further stage of the method of the present invention wherein each graft cutter has been positioned at a suitable location for cutting a respective graft.

It is preferred that the graft be cut at a location cephalic of a main side branch such as the internal iliac artery, yet that the graft be cut to have a length that permits caudal attachment to healthy tissue. This location preferably is determined using an arteriogram. The cutting device may be about 100 cm, but needs only to be somewhat longer than the delivery sheath 60L. As shown in FIG. 26, the cutting element 134 cuts the graft 66 against the stent delivery catheter 128 to separate the caudal end 86 from the portion of the graft 66 that has been anchored to the infrarenal aorta. The catheter 128 preferably has a shaft that is minimally affected by the cutting element 134. The stent catheter 128 is then withdrawn preferably to a position such that the caudel stent 130 extends partially beyond the caudal end 136 of the graft 66 (the caudal end 136 was the end formed after cutting the caudal tab 86 using the cutting elements 134). The stent 130 is then deployed, for example, by retracting a surrounding constraint to allow the stent to expand and thereby anchor the caudal end of the graft 66 in the femoral arteries. Alternately, the caudal stents 130 can be made of a deformable material such as stainless steel (for example, a Palmaz-type stent), and may be deployed by means of an inflatable balloon. In either case, the position of the caudal stents 130 is preferably determined and adjusted prior to their deployment with the assistance of a fluoroscopic image of the patient's abdominal cavity.

Once each of the stents 130 has been deployed, an arteriogram is performed to ensure that the grafts 66 are appropriately anchored to the arterial wall and that the aneurysm 40 is excluded from the circulation. As shown in FIG. 24, the D-shaped stents have their "corners" close together, which is important for excluding blood from the aneurysm. If there is some leakage into the aneurysm as detected using angiography, an appropriately sized balloon catheter (e.g. 20–26 mm diameter balloon) can be inflated in each graft (for example, sequentially) to assist the corners of the collateral of D-shaped stents 64 to come together. A successfully deployed graftstent 62 will not permit blood to enter into the aneurysmal sac 40. At the completion of the procedure, the delivery sheaths 60, and aortic guidewires 46, as well as any other devices that may remain in the patient, are removed and the incisions in the right and left femoral arteries are sutured or sealed by standard vascular surgical anastomosis techniques. The skin is then closed with standard skin closure procedures.

The invention is intended for use in deploying stents and attachment devices, i.e., devices which may be attached to a body lumen such as an artery, for example to secure a graft in place, in the vicinity of a vasculature bifurcation. As used herein, the term "stent" is intended to also include such attachment devices. The invention is not limited to any particular type of stent. A Palmaz stent, or other stent (including but not limited to self-expanding stents such as the Walsten stent (see U.S. Pat. No. 4,665,771) and stents made of shape memory alloys, e.g. Nitinol) can also be used. In place of a balloon, a mechanical deployment mechanism can be used such as described in the following Marin et al. patents: U.S. Pat. No. 5,507,769 (issued Apr. 16, 1997); U.S. Pat. No. 5,618,300 (issued Apr. 8, 1997); U.S. Pat. No. 5,591,196 (issued Jan. 7, 1997); and U.S. Pat. No. 5,443,477 (Aug. 22, 1995), each of which is hereby incorporated by reference as if set forth in their entirety herein.

As understood by those of skill in the art, a nitinol (nickel-titanium) alloy composition of approximately 55 wt. % Ni can be processed to exhibit pseudoelasticity at body temperatures. A pseudoelastic nitinol stent can be shaped to have a deployed size that is suitable for anchoring within a predetermined site (e.g., the infrarenal aorta) and then be compressed to a delivery size and held in a compressed state by a constraining sheath until the stent has been delivered to the target site. Relative motion. between the stent and the constraining sheath causes the stent to eject from the sheath and simultaneously expand to its deployed size by mechanical forces. Alternatively, a nitinol stent of desired composition can be processed so as to have a parent shape above a predetermined transition temperature (e.g., below or at body temperature) and a child shape suitable for delivery through a body passageway at temperatures below the transition temperature. Such a stent would expand in response to be thermally responsive, and can transform by virtue of the heat of the patient's body and blood, or in response to further heat provided by another source (e.g., radiation).

It is contemplated that the apparatus disclosed herein will be packaged as part of an overall system, including, one or more of the following components: delivery sheath 60, grafts 66, aortic stents 64, lead balloon catheters 68, aortic guidewires 46, bifurcation wire 48, anchor catheter 50 along with anchor lines 52, introducers 42, caudal stents 130 and their delivery catheter 128, pusher 102, anchor beads 110, anchor line cutter 108, graft cutting device 132, and snare catheters. In such a case, each delivery sheath 60 may be preloaded with a graftstent 62 (comprising a graft 66 and an aortic stent 64 ), and a lead balloon catheter 68. One of the delivery sheaths 60 may further be loaded with a snare catheter for drawing the anchor lines 52 from its distal end to -its proximal end. The caudal stents 130 can be preloaded onto delivery catheters 128, and the anchor lines 52 prewrapped on the anchor catheter 50.

From the foregoing description, it will be clear that the present invention may be embodied in other specific forms without departing from the spirit or essential characteristics thereof. The presently disclosed embodiments are therefore to be considered in all respects as illustrative and not restrictive, the scope of the invention being indicated by the appended claims, and not limited to the foregoing description.

We claim:

1. A method for endoluminally treating a pathological defect within or part of a body passageway of a patient, there being healthy tissue on a first side and on a second side of the pathological defect and the pathological defect being positioned in the vicinity of a branching passageway within a patient, comprising the steps of:

a) introducing first and second grafts through respective first and second access sites within respective delivery sheaths, each of the first and second grafts having a length and a shape memory alloy extending along the entire length thereof, the first and second access sites being on the first side of the pathological defect;

b) advancing the first and second grafts within the respective delivery sheaths until each extends across the pathological defect and is positioned in a common body passageway and on the second side of the pathological defect;

c) releasing the first and second grafts from the respective delivery sheaths with the first and second grafts opening in response to action of the shape memory alloy; each of the first and second grafts to each define a respective patent lumen free of kinks; and d) joining the first and second grafts together within the common body passageway.

2. The method as in claim 1, wherein each of the first and second grafts is folded within the respective delivery sheath.

3. The method as in claim 1, wherein the shape memory alloy comprises a first element and a second element disposed along the length of the graft, the spacing between the first element and second element being less than 1 cm.

4. The method as in claim 1, wherein the shape memory alloy is nitinol.

5. The method as in claim 1, wherein the shape memory alloy disposed along the length of the first and second grafts comprises serially spaced hoops.

6. The method as in claim 1, wherein the first and second grafts are made of a material having the shape memory alloy included in the weave thereof.

7. The method as in claim 1, wherein the shape memory alloy comprises resiliently deformable hoops.

8. The method as in claim 1, wherein the joining step comprises endoluminally tying the first and second grafts together.

9. The method as in claim 1, including the additional step of affixing one end of an anchor line to the first graft prior to the step of introducing the first graft through the first access site.

10. The method as in claim 9, including the additional step of drawing a second end of the anchor line through the second access site.

11. The method as in claim 10, including the additional step of threadedly coupling the second graft to the anchor line prior to the step of introducing the second graft through second access site.

12. The method as in claim 11, wherein the step of joining the first and second grafts includes the step of advancing one of a knot and an anchor bead over the second end of the anchor line to the second side of the pathological defect.

13. The method as in claim 12, including the additional step of rotationally aligning the first and second grafts by reducing the length of anchor line extending between the first and second grafts at the second side of the pathological defect.

14. The method as in claim 9, wherein there are plural anchor lines each having one end and a second end and wherein the affixing step includes affixing the one end of the plural anchor lines to the first graft, and wherein the second end of the plural anchor lines are drawn through the second access site.

15. The method as in claim 14, including the additional step of threadedly coupling the second ends of each of the plural anchor lines to the second graft prior to the step of introducing the second graft through the second access site.

16. The method as in claim 15, wherein the step of joining the first and second grafts includes the step of advancing one of a knot and an anchor bead over each of the second ends of the plural anchor lines to the second side of the pathological defect.

17. The method as in claim 1, wherein the shape memory alloy of the first and second grafts include preset bows which substantially mate upon joining the first and second grafts on the second side of the pathological defect.

18. The method as in claim 1, wherein the joining step comprises drawing a cephalic portion of the two grafts together.

19. The method as in claim 1, including the additional step of affixing the first and second grafts within the common body passageway on the second side of the pathological defect whereby the pathological defect is excluded.

20. A method for endoluminally treating a pathological defect within or part of a body passageway of a patient, there being healthy tissue on a first side and on a second side of the pathological defect and the pathological defect being positioned in the vicinity of a branching passageway within a patient, comprising the steps of:

a) introducing first and second grafts through respective first and second access sites within respective delivery sheaths, each of the first and second grafts having a length and a shape memory alloy extending along the entire length thereof, the first and second access sites being on the first side of the pathological defect;

b) advancing the first and second grafts within the respective delivery sheaths until each extends across the pathological defect and is positioned in a common body passageway and on the second side of the pathological defect;

c) releasing the first and second grafts from the respective delivery sheaths with the first and second grafts opening in response to action of the shape memory alloy; each of the first and second grafts to each define a respective patent lumen free of kinks; and d) attaching the first and second grafts together within the common body passageway.

* * * * *